(12) United States Patent
Sandsten et al.

(10) Patent No.: US 10,416,076 B2
(45) Date of Patent: *Sep. 17, 2019

(54) QUANTIFYING GAS IN PASSIVE OPTICAL GAS IMAGING

(71) Applicant: FLIR Systems AB, Täby (SE)

(72) Inventors: Jonas Sandsten, Lomma (SE); Jonce Kotaleski, Stocksund (SE); Erik Ekerot, Solna (SE)

(73) Assignee: FLIR SYSTEMS AB, Täby (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/693,007

(22) Filed: Aug. 31, 2017

(65) Prior Publication Data

US 2017/0363541 A1 Dec. 21, 2017

Related U.S. Application Data

(63) Continuation of application No. PCT/EP2016/000363, filed on Mar. 2, 2016.

(60) Provisional application No. 62/127,264, filed on Mar. 2, 2015.

(51) Int. Cl.
*G01N 21/3518* (2014.01)
*G01N 21/3504* (2014.01)
*G06T 5/50* (2006.01)

(52) U.S. Cl.
CPC ..... *G01N 21/3518* (2013.01); *G01N 21/3504* (2013.01); *G06T 5/50* (2013.01); *G01N 2021/3531* (2013.01); *G06T 2207/10048* (2013.01); *G06T 2207/20224* (2013.01)

(58) Field of Classification Search
CPC .................................................. G01N 21/3518
See application file for complete search history.

(56) References Cited

U.S. PATENT DOCUMENTS

| 5,430,293 | A | * | 7/1995 | Sato | G01M 3/38 |
| | | | | | 250/330 |
| 2005/0134859 | A1 | * | 6/2005 | Kalayeh | G01N 21/31 |
| | | | | | 356/437 |
| 2006/0091310 | A1 | * | 5/2006 | Furry | G01J 5/061 |
| | | | | | 250/330 |

(Continued)

FOREIGN PATENT DOCUMENTS

WO WO-03044499 A2 * 5/2003 .............. G01M 3/38

OTHER PUBLICATIONS

Messinger, "A method for quantification of gas plumes in thermal hyperspectral imagery", Jun. 2005, Proc. SPIE 5806, Algorithms and Technologies for Multispectral, Hyperspectral, and Ultraspectral Imagery XI, pp. 218-228 (Year: 2005).*

(Continued)

*Primary Examiner* — David P Porta
*Assistant Examiner* — Jeremy S Valentiner
(74) *Attorney, Agent, or Firm* — Haynes and Boone, LLP

(57) ABSTRACT

A method and a system to quantify gas in a thermal imaging device, said method comprising obtaining a gas-absorption-path-length image as a scene difference infrared image based on a gas infrared image and a scene background infrared image substantially depicting the same scene and generating a quantified scene difference infrared image based on said scene difference infrared image and a predefined gas-quantifying relation.

20 Claims, 17 Drawing Sheets

(56) References Cited

U.S. PATENT DOCUMENTS

| | | | | |
|---|---|---|---|---|
| 2008/0283753 A1* | 11/2008 | Jensen | ............... | G01J 3/36 |
| | | | | 250/339.02 |
| 2013/0113939 A1* | 5/2013 | Strandemar | ............... | G06T 5/10 |
| | | | | 348/164 |
| 2016/0238451 A1* | 8/2016 | Zeng | ............... | G06T 7/11 |

OTHER PUBLICATIONS

Alazarine et al.—WO 03/044499 A2—English Translation—Google Patents obtained May 3, 2019 (Year: 2019).*

Messinger, David, "A method for quantification of gas plumes in thermal hyperspectral imagery", Algorithma NS Technologies for Multispectral, Hyperspectral, and Ultraspectral Imagery XI, 2005, pp. 218-228, Proceedings of SPIE vol. 5806, SPIE, Bellingham, WA.

Gross et al., "Remote Identification and Quantification of Industrial Smokestack Effluents via Imaging Fourier-Transform Spectroscopy", Environmental Science & Technology, Dec. 15, 2010, pp. 9390-9397, vol. 44, No. 24, American Chemical Society, Washington, D.C.

* cited by examiner

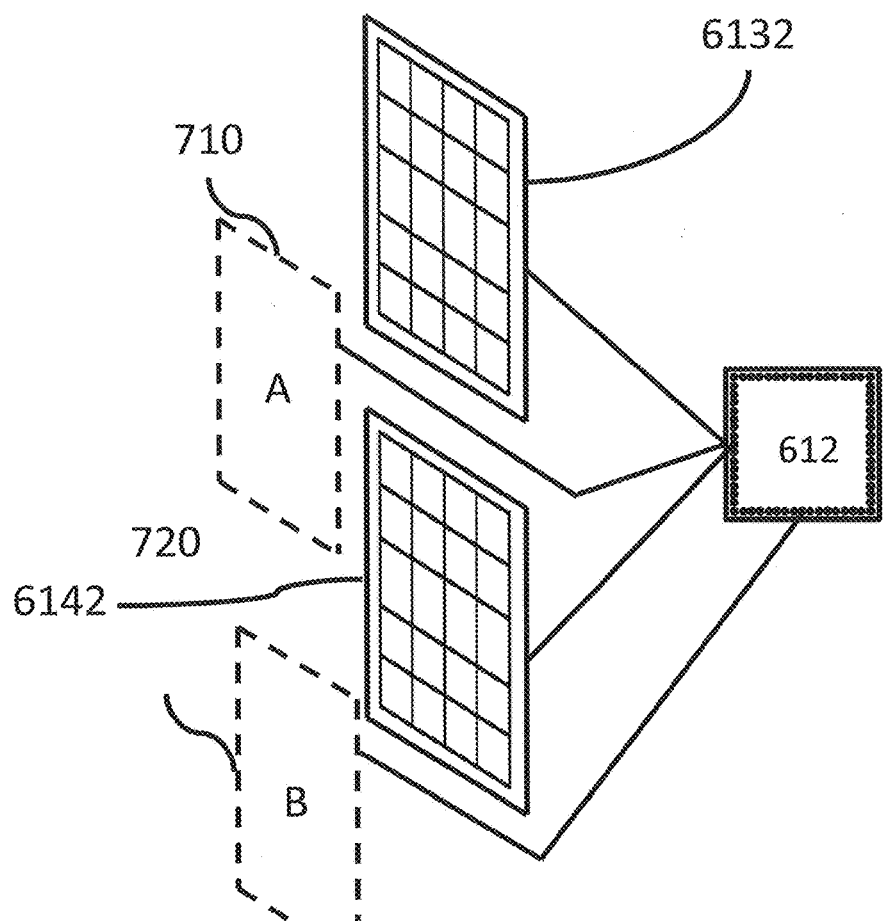
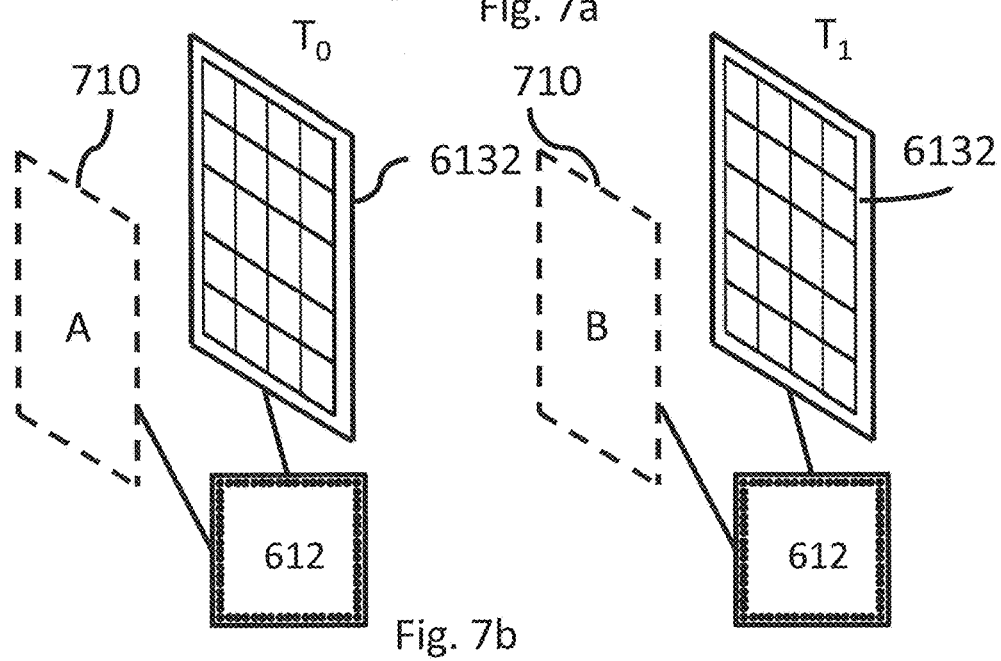
Fig. 7a
Fig. 7b

Fig. 17

| Concentration-length | Simulated temperature |
|---|---|
| 1000ppmm | 73.0159°C |
| 5000ppmm | 70.3222°C |
| 10000ppmm | 68.4830°C |
| 20000ppmm | 66.1178°C |
| 30000ppmm | 64.4258°C |
| 60000ppmm | 60.9544°C |
| 120000ppmm | 56.9215°C |
| 200000ppmm | 53.7470°C |

180 GQR, Table 1

| Known concentration-length $CL_K$ | Measured temperature T | Measured concentration-length $CL_M$ | $CL_M/CL_K$ |
|---|---|---|---|
| 5 000 ppmm | 68.7°C | 9 090 ppmm | 1.82 |
| 10 000 ppmm | 66.7°C | 17 190 ppmm | 1.72 |
| 20 000 ppmm | 63.8°C | 34 270 ppmm | 1.71 |
| 30 000 ppmm | 61.7°C | 52 020 ppmm | 1.73 |
| 60 000 ppmm | 57.9°C | 102 180 ppmm | 1.70 |
| 120 000 ppmm | 53.7°C | 201 630 ppmm | 1.68 |

180 GQR, Table 2

| Concentration-length | Simulated temperature |
|---|---|
| 1000ppmm | 73.159°C |
| 5000ppmm | 70.3222°C |
| 10000ppmm | 68.4830°C |
| 20000ppmm | 66.1178°C |
| 30000ppmm | 64.4258°C |
| 60000ppmm | 60.9544°C |
| 120000ppmm | 56.9215°C |
| 200000ppmm | 53.7470°C |

180 GQR, Table 3

| Known concentration-length $CL_K$ | Measured temperature T | Measured concentration-length $CL_M$ | $CL_M/CL_K$ |
|---|---|---|---|
| 5 000 ppmm | 66.7°C | 48 630 ppmm | 9.73 |
| 10 000 ppmm | 66.1°C | 72 860 ppmm | 7.29 |
| 20 000 ppmm | 64.9°C | 156 040 ppmm | 7.80 |
| 30 000 ppmm | 64.5°C | 198 770 ppmm | 6.63 |
| 60 000 ppmm | 63.2°C | 416 940 ppmm | 6.95 |
| 120 000 ppmm | 61.9°C | 811 570 ppmm | 6.76 |

180 GQR, Table 4

QUANTIFYING GAS IN PASSIVE OPTICAL GAS IMAGING

CROSS-REFERENCE TO RELATED APPLICATIONS

This application is a continuation of International Patent Application No. PCT/EP2016/000363 filed Mar. 2, 2016 and entitled "QUANTIFYING GAS IN PASSIVE OPTICAL GAS IMAGING," which is incorporated herein by reference in its entirety.

International Patent Application No. PCT/EP2016/000363 filed Mar. 2, 2016 claims priority to and the benefit of U.S. Provisional Patent Application No. 62/127,264 filed Mar. 2, 2015 and entitled "QUANTIFYING GAS IN PASSIVE OPTICAL GAS IMAGING," which is hereby incorporated by reference in its entirety.

TECHNICAL FIELD

The present disclosure relates generally to imaging and visualizing gas and, in particular, to imaging and visualizing quantified gas using infrared imaging systems and methods.

BACKGROUND

Thermal, or infrared (IR), images of scenes are often useful for monitoring, inspection and/or maintenance purposes, e.g. for monitoring gas leaks at an industrial plant. Typically, a thermal imaging device, e.g. in the form of a thermography arrangement or an infrared IR camera, is provided to capture infrared (IR) image data values, representing infrared radiation emitted from an observed scene. The captured IR image can after capturing be processed, displayed and/or saved, for example in the thermal imaging device or in a computing device connected to the thermal imaging device such as a tablet computer, a smartphone, a laptop or a desktop computer.

Thermal imaging devices, such as IR cameras, might be used for detecting gas occurrence, for example in the form of a gas cloud or gas plume e.g. from fugitive gas emissions or gas leaks, and for producing a visual representation of such gas occurrence as a gas image. Such a gas image can be used for visualizing gas occurrence or gas leaks, e.g. as smoke or a cloud on images presented on the viewfinder of a camera, on an integrated or separate display, or on an external computing device, thereby allowing the user to see gas occurrence in a scene observed and imaged by means of an IR camera. A variant of such techniques is called passive infrared gas imaging and is based on using radiation from a scene without any additional illumination for detecting gas.

However, a problem with conventional systems is that the sensitivity of the thermal imaging device might be too low to detect gas below a certain gas particle concentration or, in other words, the contrast between gas information and noise/interference in a generated gas image is too low to identify gas. Another problem is that the sensitivity is further reduced by various physical aspects, such as varying temperatures and emissivity in the observed scene background, noise, other gases, aerosol particles and moving gas clouds.

In conventional technology, particularly using cooled thermal imaging devices, gas imaging may be based on the difference in absorption or transmission of infrared radiation in different wavelength bands. A problem, particularly with uncooled thermal imaging devices, is that when basing gas imaging on the difference in absorption or transmission of infrared radiation in selected wavelength bands, the bands cannot be made narrow due to high noise contribution by imaging device components such as filters, optical systems, wave guide and the detector itself. This means that physical characteristics of the system, such as noise or thermal interference might vary significantly with wavelength and will be more difficult to compensate for.

In conventional systems, particularly using cooled thermal imaging devices, gas imaging may be based on the difference in absorption or transmission of infrared radiation in different wavelength bands. A problem, particularly with uncooled thermal imaging devices, is that when basing gas imaging on the difference in absorption or transmission of infrared radiation in selected wavelength bands, the sensitivity of the thermal imaging device might be too low to quantify gas below a certain gas concentration or in other words the contrast between gas information and noise/interference in a generated gas infrared image is too low to quantify gas.

Therefore, there is a need to address the problems of conventional systems to improve quantify gas in passive imaging.

SUMMARY

Various techniques and embodiments of methods, systems and computer program products are disclosed for quantifying gas in the imaging of gas in a scene having a background and a possible occurrence of gas. In various embodiments quantification of gas is carried out by obtaining a gas-absorption-path-length image as a scene difference infrared image based on a gas infrared image and a scene background infrared image substantially depicting the same scene. A quantified scene difference infrared image is then generated based on said scene difference infrared image and a predefined gas-quantifying relation GQR.

In further variants, in accordance with one or more embodiments, the methods, systems and computer program products further comprise a selection of:
  Generating a quantified scene difference infrared image, wherein the gas-quantifying relation describes the relation between scene difference infrared image pixel values and quantified scene difference infrared image pixel values in the form of a concentration length product expressed in parts per million*meter or ppm*m.
  Generating a gas-quantifying relation by measuring a first set of quantified scene difference infrared image pixel values for known gas concentration, gas-absorption path length, gas temperature and background temperature and expanding said first set to a second larger set by applying curve fitting techniques.
  Obtaining a gas-absorption-path-length image further comprising:
    determining a high absorption wavelength band A and a low absorption wavelength band B to improve contrast in a generated gas-absorption-path-length image based on estimated image noise, a predetermined absorption spectrum of the gas, an estimated gas temperature and an estimated background temperature, wherein high absorption wavelength band A includes an absorption wavelength band G from the absorption spectrum and wherein low absorption wavelength band B at least partially overlaps high absorption wavelength band A;
    generating infrared imaging system control data to control the capturing, by an infrared imaging system, of a gas infrared image of a scene comprising intensity of infrared radiation within high absorption wavelength band A and of a background infrared image of the scene comprising intensity of infrared radiation within low absorption wavelength band B;

generating a gas-absorption-path-length image based on the gas infrared image and the background infrared image.

Providing an estimated image noise comprising a Noise Equivalent Temperature Difference, wherein the quantified scene difference infrared image pixel values comprise temperature values, e.g. in degrees Celsius or Kelvin.

Determining a high absorption wavelength band A with a lower endpoint in the interval of [6-7.8 μm]-[8-9.6 μm]] and wherein wavelength band A 510 is determined with a higher endpoint in the interval of [8-9.6 μm].

Obtaining a gas-absorption-path-length image further comprising:
  determining a water related wavelength band C to improve contrast in a generated gas-absorption-path-length image based on a predetermined water absorption spectrum, wherein water related wavelength band C includes at least a local maximum of the water absorption spectrum and excludes high absorption wavelength band A and low absorption wavelength band B;
  generating infrared imaging system control data to control the capturing of a water infrared image of the scene by an infrared imaging system, wherein the water infrared image comprises intensity of infrared radiation within the water related wavelength band C;
  wherein generating a quantified scene difference infrared image is further based on the water infrared image.

A thermal imaging device to quantify gas in the imaging of a scene having a background and a possible occurrence of gas, said device comprising an infrared (IR) imaging system, a memory and a processor being adapted to perform any of the steps and functions of embodiments described herein.

A computer-readable medium for quantifying gas in the imaging of a scene having a background and a possible occurrence of gas, comprising stored thereon:
  non-transitory information for performing any of the embodiments described herein;
  and/or
  non-transitory information configured to control a processor/processing unit to perform any of the steps or functions described herein.

A computer program product for quantifying gas in the imaging of a scene having a background and a possible occurrence of gas, comprising code portions adapted to control a processor to perform any of the steps or functions of any of the embodiments described herein.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 7a shows a schematic view of a spatial sensor configuration in a thermal imaging device, in accordance with one or more embodiments of the disclosure.

FIG. 7b shows a schematic view of a temporal sensor configuration in a thermal imaging device, in accordance with one or more embodiments of the disclosure.

FIG. 17 shows a Gas-Quantifying Relation 180 exemplified in table 1-4, in accordance with one or more embodiments of the disclosure.

Embodiments of the present disclosure and their advantages are best understood by referring to the detailed description that follows. It should be appreciated that like

DETAILED DESCRIPTION

Introduction

The disclosure relates to imaging and visualizing quantified gas using infrared IR sensors or detectors and image processing. An example of a use case is the inspection with a thermal imaging device of a part of an industrial complex handling gas.

Figure 1:
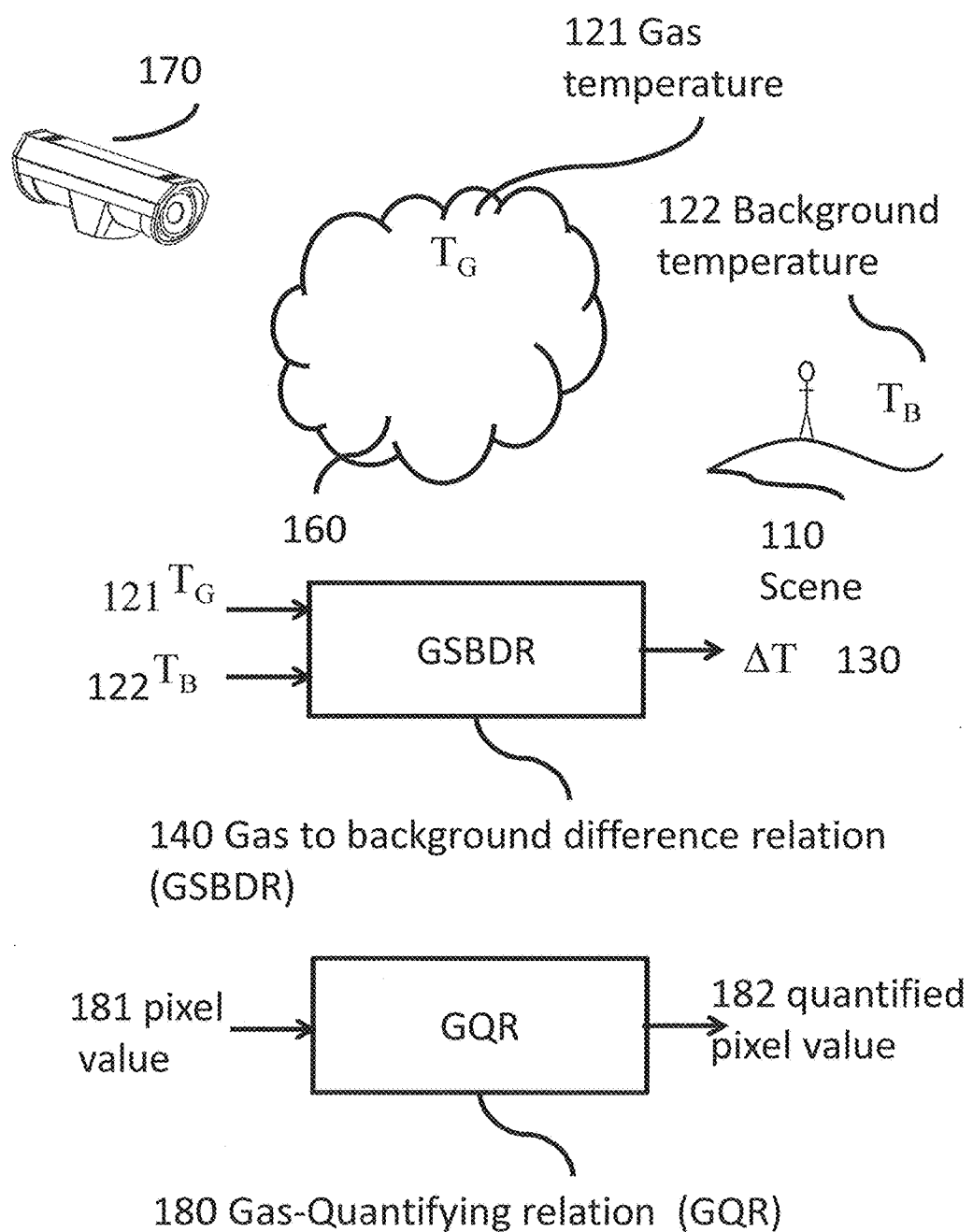
FIG. 1 shows a schematic view of passive imaging of gas based on a background temperature difference ΔT, in accordance with of one or more embodiments of the disclosure.

In particular the disclosure relates to passive gas imaging that uses thermal background radiation within the infrared region and can be used to image gas for example against a cold background, in this case imaging thermal emission or radiation from the gas, or used against a warm background, in that case imaging absorption by the gas of thermal radiation from the background. Imaging of gas is based on the difference in gas temperature $T_G$ and background temperature $T_B$, hereinafter referred to as gas to background temperature difference $\Delta T$. However, the sensitivity of a thermal imaging system is dependent on the difference in gas temperature $T_G$ and background temperature $T_B$, FIG. 1 shows a schematic view of a method and an apparatus for passive imaging of gas based on background temperature difference $\Delta T$ 130, in accordance with one or more embodiments. A thermal imaging device 170 is adapted to capture radiation within controllable wavelength bands and thus to produce infrared images, herein also called IR images or thermal images, representing a particular selected wavelength band of infrared radiation from a scene. Between the thermal imaging device 170 (also referred to as a thermal imaging system) and a scene background 110 there is gas 160 present, e.g. in a gas cloud with a gas concentration in parts per million ppm and with the width along the path from the scene 110 to the thermal imaging device 170 of a gas-absorption path-length 1601, in the form of aerosol particles or gas molecules, in the figures illustrated as a gas occurrence in the shape of a gas cloud. The scene background 110 has a background temperature TB 122, and the gas has a gas temperature TG 121. A temperature difference parameter preferably in the form of a gas to background temperature difference $\Delta T$ 130 can be determined or calculated based on the background temperature TB 122 and the gas temperature TG 121 by a gas to background difference relation 140. In accordance with one or more embodiments, a thermal imaging device 170 is configured and/or controlled to capture and/or generate a selection of inter alia a background IR image representing the thermal radiation from the background in a scene, a gas IR image representing a gas occurrence between the thermal imaging device and a background in a scene and/or a possible other IR image representing other phenomena in the scene.

In one or more embodiments, a gas-absorption-path-length image representing the length of the path of radiation from the scene background 110 through a gas occurrence in the scene can be generated based on a gas infrared image, a background infrared image and optionally the background temperature difference $\Delta T$ 130. In yet an embodiment a pixel value 181 derived from processed pixel values in a gas-absorption-path-length image is at least used to determine a quantified pixel value 182 indicative of concentration length by gas-quantifying relation GQR 180 in the form of a concentration length or concentration-path length product CL in parts per million*meter ppm*m. In yet an embodiment, quantified gas is visualized in a quantified gas visualization image presentable or presented to the user on a display, this image being based on pixel values of the gas-absorption-path-length image. In yet an embodiment a background temperature $T_B$ 122 derived from a pixel value in a background infrared image and a gas temperature $T_G$ 121 derived from a pixel value in a gas infrared image are used to determine the background temperature difference $\Delta T$ 130.

In one or more embodiments, the gas temperature $T_G$ is estimated based on a measured ambient air temperature retrieved from an ambient air temperature sensor and/or based on a previously captured gas IR image that comprises a representation of the intensity of infrared radiation within a first wavelength band A substantially including wavelengths of infrared radiation with high absorptance values for the gas in an absorption spectrum and/or low transmittance values in a transmission spectrum. In other words, the first wavelength band A is a high absorption wavelength band that includes wavelengths significantly affected by the presence of the gas to be imaged. In a case where the gas has a temperature higher than the ambient air temperature or the background temperature there is radiation from the gas in an emission spectrum. The first wavelength band A is herein also called high absorption wavelength band A.

In one or more embodiments, the background temperature $T_B$ is estimated based on a previously captured background IR image that comprises a representation of the intensity of infrared radiation within a second wavelength band B substantially including wavelengths of infrared radiation with low absorptance values for the gas in an absorption spectrum and/or high transmittance values in a transmission spectrum. In other words, the second wavelength band B is a low absorption wavelength band and/or a high transmission wavelength band that includes wavelengths insignificantly affected by the presence of the gas to be detected. The second wavelength band B is herein also called low absorption wavelength band B.

Figure 2A:
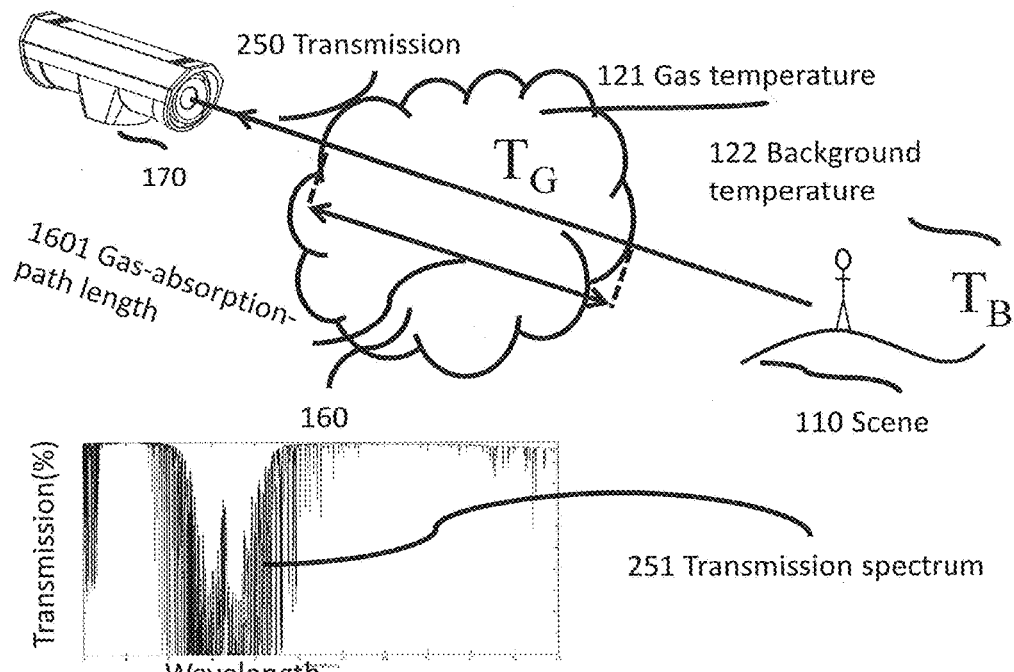
FIG. 2a illustrates a method for imaging gas, in accordance with one or more embodiments of the disclosure.

FIG. 2a illustrates a method for imaging gas in accordance with one or more embodiments for example applicable in a situation where the background temperature $T_B$ 122 is higher than the gas temperature $T_G$ 121, i.e. the scene background is warmer than the gas 160. A fraction of the energy or infrared radiation emitted from the scene background 110 is transmitted through the gas 160, indicated as radiation transmission 250 with a gas-absorption-path length 1601, to the detector in a thermal imaging device 170. In one or more embodiments this fraction can be determined by using a predetermined relation for example based on a transmission spectrum 251.

Figure 2B:
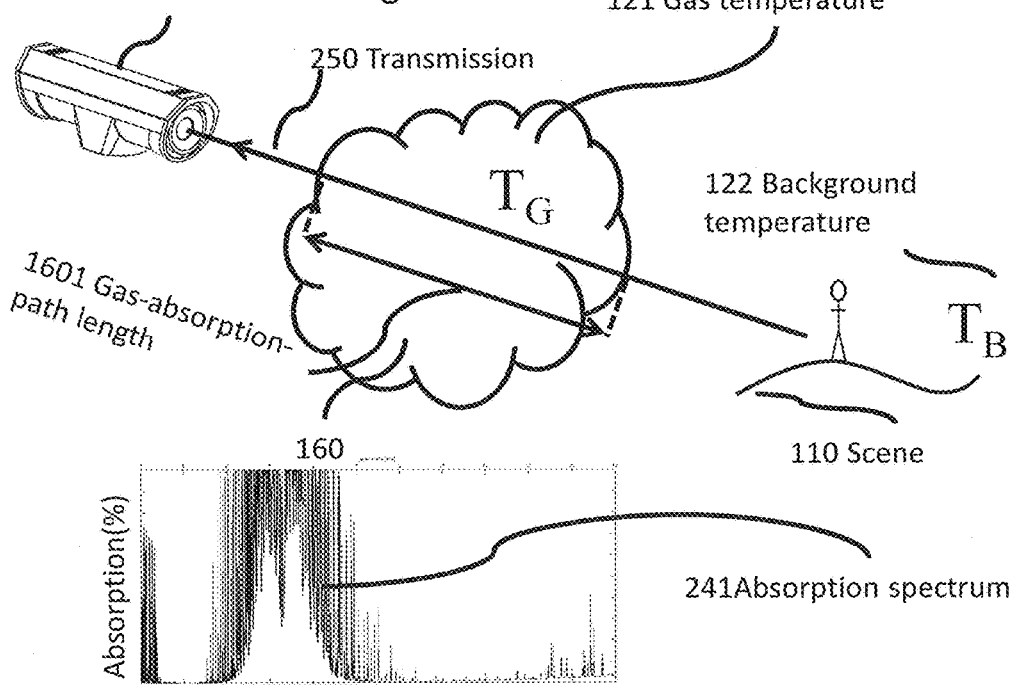
FIG. 2b illustrates a further method for imaging gas, in accordance with one or more embodiments of the disclosure.

FIG. 2b illustrates a method for imaging gas in accordance with one or more embodiments for example applicable in a situation where the background temperature $T_B$ 122 is lower than the gas temperature $T_G$ 121, i.e. the scene background is colder than the gas. A fraction of the energy or infrared radiation emitted from the scene background 110 is transmitted through the gas, indicated as radiation transmission 250 with a gas-absorption-path length 1601, to the detector in a thermal imaging device 170. In one or more embodiments this transmitted fraction can be determined by using a predetermined relation for example based on an absorption spectrum 241.

By controlling the thermal imaging system to capture radiation in a high absorption wavelength band A including wavelengths significantly affected by the presence of the gas to be detected, and to capture radiation in a low absorption wavelength band B including wavelengths insignificantly affected by the presence of the gas to be detected, a background IR image and a gas IR image are generated. Based on the background IR image, on the gas IR image and dependent on a transmission spectrum 251 and/or on an absorption spectrum 241, a gas-absorption-path-length image with improved contrast is generated in a system with improved sensitivity and/or improved signal to noise ration.

Figure 3:
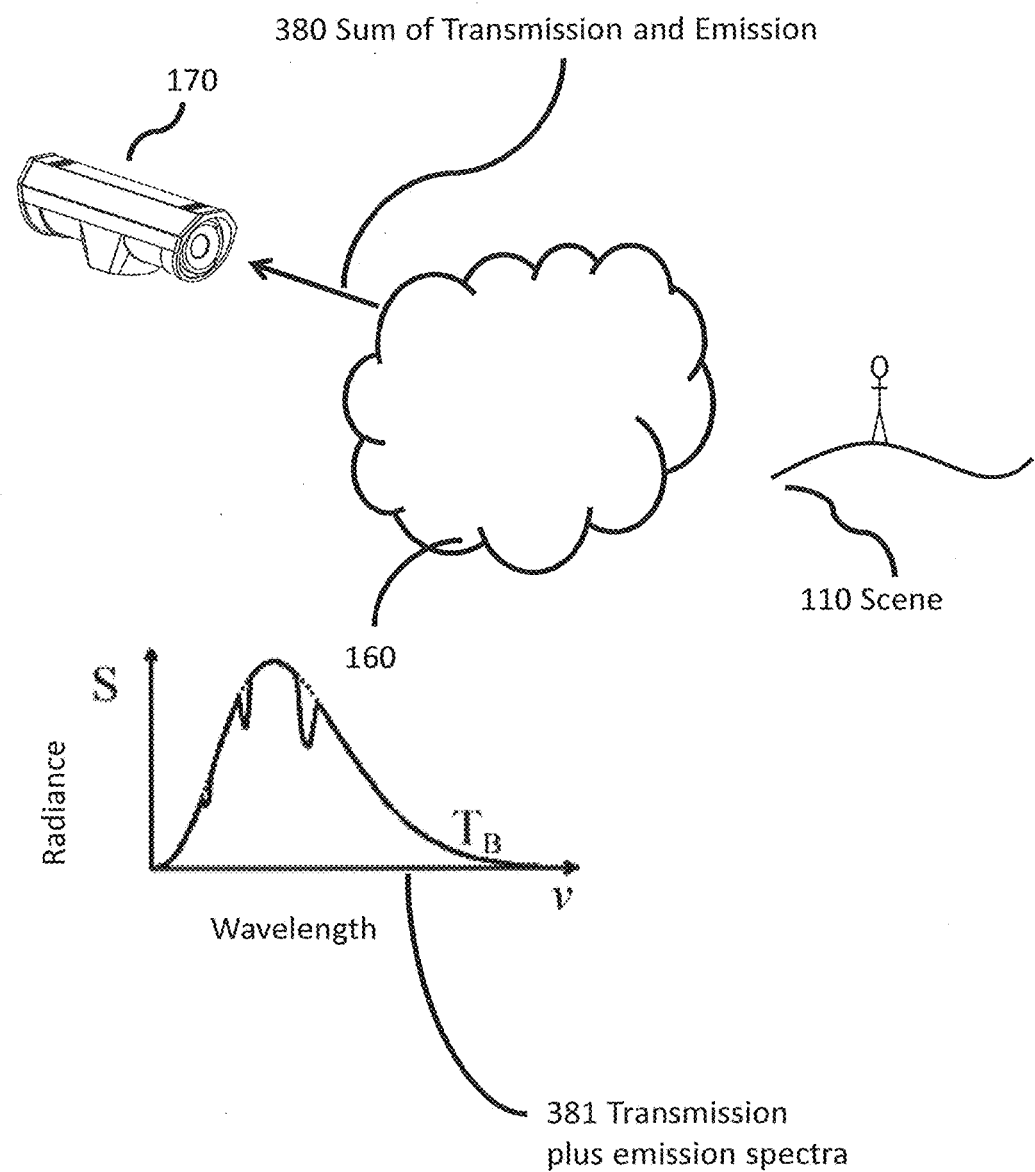
FIG. 3 illustrates a method for imaging gas in a case when the background temperature TB is lower than the gas temperature TG, in accordance with one or more embodiments of the disclosure.

FIG. 3 illustrates one or more embodiments applied in a situation where the background temperature $T_B$ is lower than the gas temperature $T_G$, i.e. the background is colder than the gas 160. The thermal imaging system 170 is controlled to capture radiation in a low absorption wavelength band B including wavelengths less affected or not so affected, i.e. insignificantly affected by the presence of the gas to be detected, and to capture radiation in a high absorption wavelength band A including wavelengths more affected, i.e. significantly affected by the presence of the gas to be detected. There is also radiation emitted from the gas 160 in wavelengths in an emission spectrum. The thermal imaging system is controlled to capture radiation comprising a sum 380 of transmission through the gas and emission from the gas 160. A gas-absorption-path-length image is generated based on a transmission plus emission spectrum 381 being a sum of a transmission spectrum and an emission spectrum.

Figure 4:
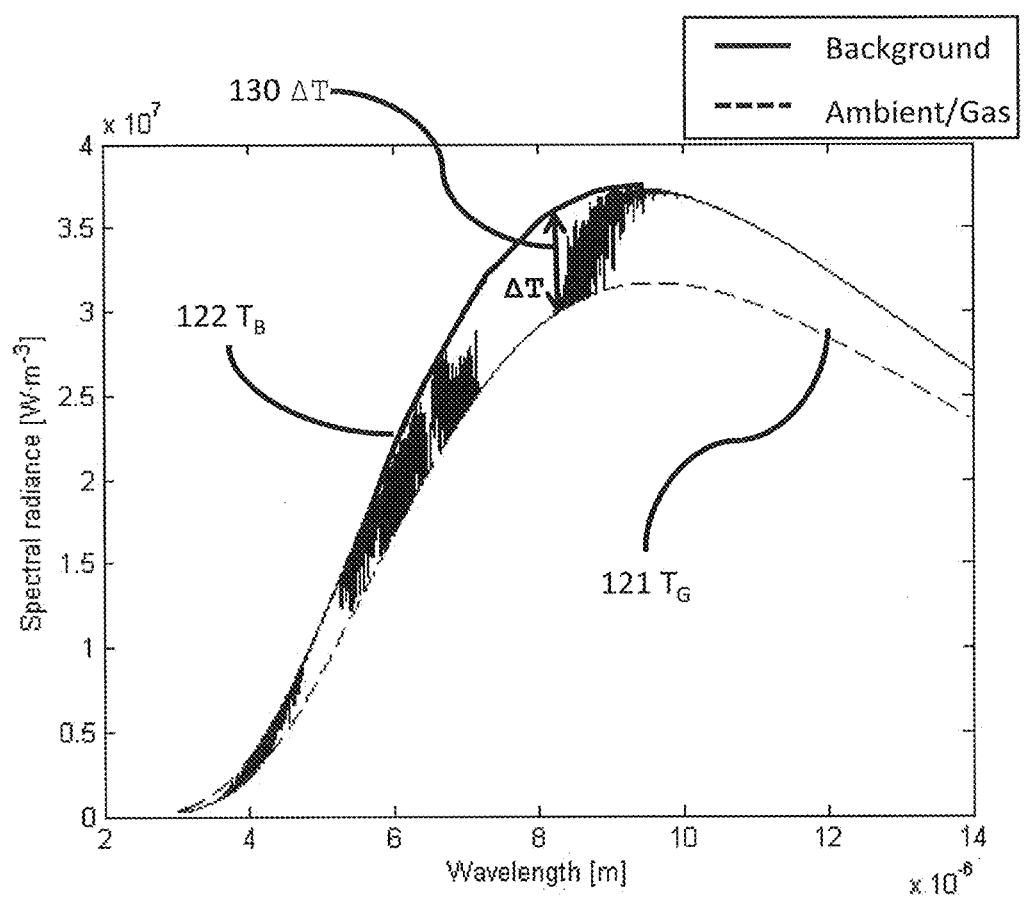
FIG. 4 illustrates in a graph an example on how gas temperature TG, background temperature TB and gas to background temperature difference ΔT varies with the wavelength of the infrared radiation from a scene having a gas occurrence.

FIG. 4 is a graph showing radiance from a scene in relation to wavelength in the infrared range, the scene comprising a background and a gas occurrence in the ambient atmosphere in the scene. Translated to temperature corresponding to the radiance related to wavelength, this graph shows an example on how the gas temperature $T_G$ indicated with an intermittently drawn line, the background temperature $T_B$ indicated with a fully drawn line and the gas to background temperature difference $\Delta T$ 130, i.e. the difference $T_B$-$T_G$, varies with the wavelength of the infrared radiation from the scene.

Figure 5:
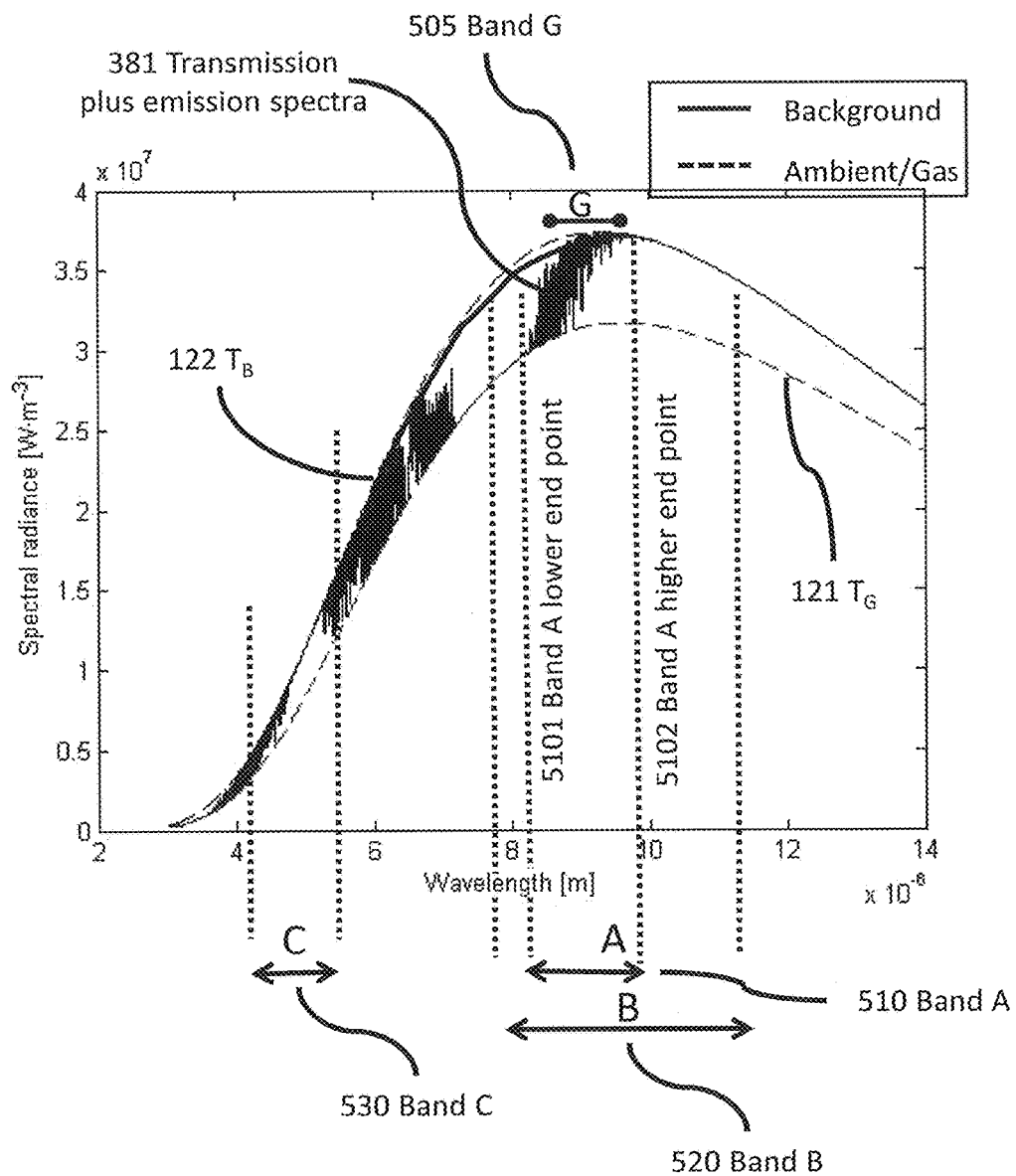
FIG. 5 illustrates in a graph an example of a wavelength band A 510 and a wavelength band B 520 determined to improve contrast in a generated gas-absorption-path-length image, in accordance with one or more embodiments of the disclosure.

FIG. 5 illustrates by means of a temperature/wavelength relation similar to that of FIG. 4 an example of one or more embodiments wherein a high absorption wavelength band A 510 and a low absorption wavelength band B 520 have been determined for the purpose to improve contrast in a generated gas-absorption-path-length image based on a predetermined absorption spectrum 241 of the gas, an estimated gas temperature $T_G$ 121 and an estimated background temperature $T_B$ 122. Wavelength band B 520 is selected to include wavelengths less affected or not so affected, i.e. insignificantly affected by the presence of the gas to be detected. Wavelength band A 510 is selected to include wavelengths more or strongly affected, i.e. significantly selected by the presence of the gas to be detected. In one or more embodiments, wavelength band A 510 includes an absorption wavelength band G 505 from the absorption spectrum 241 (FIG. 2b), i.e. a subset of the absorption spectrum significantly affected by the presence of the gas to be imaged, or expressed in a different aspect as a subset of a transmission spectrum less affected by the presence of the gas to be imaged. Furthermore, the low absorption wavelength band B 520 at least partially overlaps wavelength band A 510, thereby minimizing variations between wavelength band A 510 and wavelength band B 520 in emission/emissivity represented by values in the emission spectrum. Thereby an improved sensitivity and an improved signal to noise ratio is achieved in the thermal imaging system resulting in improved contrast in a generated gas-absorption-path-length image. Another effect by one or more embodiments is an elimination or simplification of the complexity of compensating for varying emission/emissivity in a scene.

System Embodiments

Figure 6:
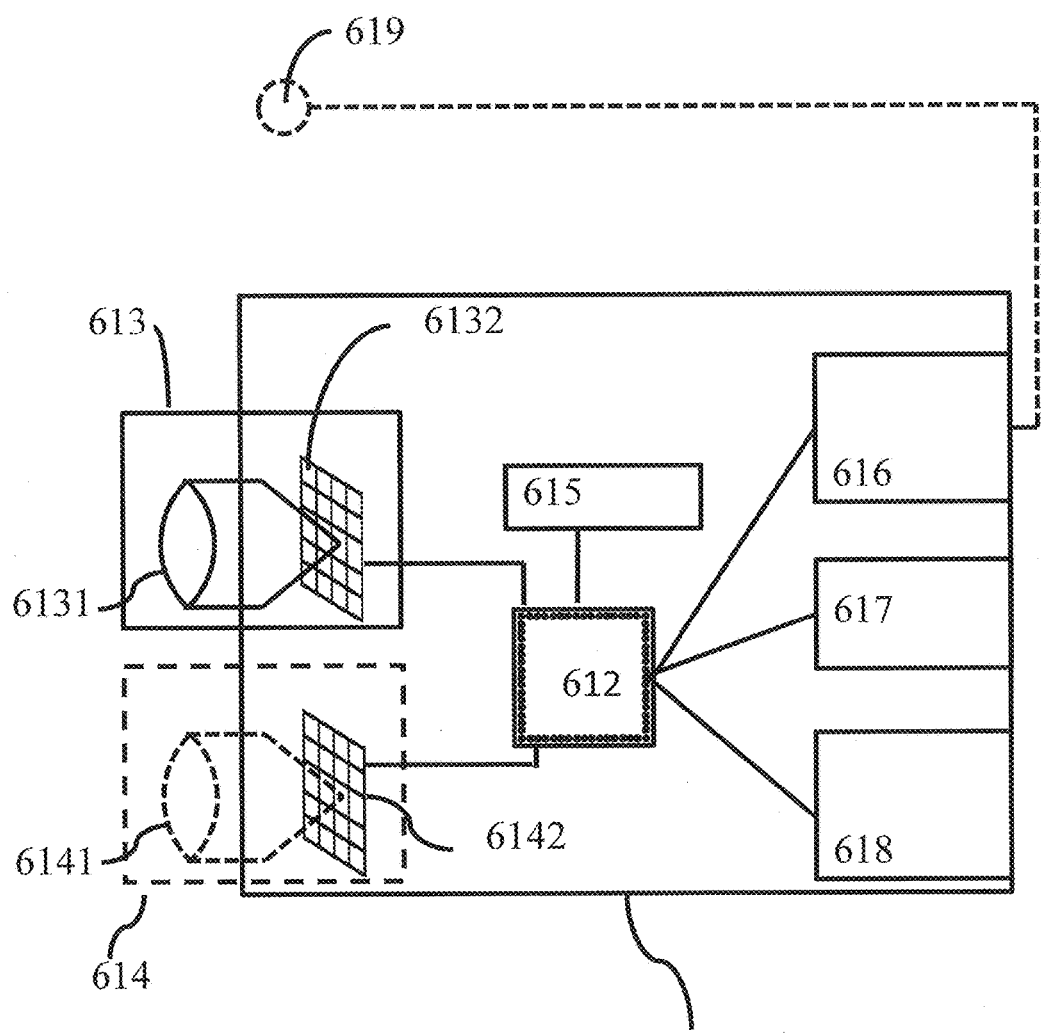
FIG. 6 shows a schematic view of a thermal imaging device, in accordance with one or more embodiments of the disclosure.

FIG. 6 shows a schematic view of one or more embodiments of a thermal imaging device or system 170, e.g. in the form of a thermography arrangement or an infrared IR camera.

In embodiments, the thermal imaging device 170 comprises a processor 612

In embodiments, the thermal imaging device 170 comprises a first infrared (IR) imaging system 613 that is configured and/or controllable to capture infrared (IR) images in the form of IR image data values/pixel values, representing infrared radiation emitted from an observed scene within one or more selectable wavelength bands A, B or C. The infrared (IR) imaging system 613 is further communicatively coupled to a processor 612.

The first infrared (IR) imaging system 613 is further configured to receive control data and to trigger the capturing of an IR image of a scene within a selected wavelength band in response to said control data. The first infrared (IR) imaging system 613 is further arranged to send a signal frame or data frame of IR image data values representing a captured image to the processor 612. IR image data typically include data values for example represented in an instance of a data structure, such as an image data frame as mentioned. In embodiments, the processor/processing unit 612 is provided with specifically designed programming or program code portions adapted to control the processing unit to perform the steps and functions of one or more embodiments of the method and/or methods described herein.

The thermal imaging device 170 further comprises at least one memory 615 configured to store data values or parameters received from a processor 612 or to retrieve and send data values or parameters to a processor 612. A communications interface 616 is configured to send or receive data values or parameters to or from a processor 612 to or from external or internal units or sensors via the communications interface 616. An optional input device 617 is configured to receive an input or an indication from a user, e.g. an input of a user indicating a command to execute the imaging of a gas-absorption-path-length image.

In one or more embodiments, the thermal imaging device 170 further comprises a display 618 configured to receive a signal from a processor 612 and to display the received signal as a displayed image, e.g. to display a visual representation of a gas-absorption-path-length image to a user of the thermal imaging device 170. In one or more embodiments, the display 618 is integrated with a user input device 617 configured to receive a signal from a processor 612 and to display the received signal as a displayed image and receive input or indications from a user, e.g. by comprising touch screen functionality and to send a user input signal to said processor/processing unit 612.

In one or more embodiments, the thermal imaging device 170 further comprises an ambient air temperature sensor 619 configured to measure ambient air temperature and generate an ambient air temperature data value and provide the ambient air temperature data value to the processor 612 receiving, polling or retrieving the ambient air temperature data value. In one or more embodiments, the ambient air temperature sensor 619 is communicatively coupled to the processor 612 directly or via the communications interface 616, and may be provided as an external or an internal unit.

In one or more embodiments, the thermal imaging device 170 further optionally comprises a second infrared (IR) imaging system 614, preferably with properties and functions similar to those of the first infrared (IR) imaging system 612 described above. The second infrared (IR) imaging system 614 is similarly configured and/or controllable to capture infrared (IR) images in the form of IR image data values/pixel values, representing infrared radiation emitted from an observed scene within one or more selectable wavelength bands A, B or C. The second infrared (IR) imaging system 614 is further communicatively coupled to a processor 612, and is further configured to receive control data and to trigger the capturing of an IR image of a scene within a selected wavelength band in response to said control data. The second infrared (IR) imaging system 614 is further arranged to send a signal frame of IR image data values representing an infrared (IR) image to the processor 612.

Typically, the described infrared (IR) imaging systems 613, 614 each comprises an infrared (IR) optical system 6131, 6141, e.g. comprising a lens, possible zoom functionality and focus functionality 6131, together with a corresponding infrared (IR) sensor 6132, 6142, for example comprising a micro-bolometer focal plane array.

Examples of Controllable/Selectable Wavelength Bands

The described infrared (IR) imaging systems 613, 614 are configured and/or controllable to capture infrared (IR) images in the form of IR image data values/pixel values, representing infrared radiation emitted from an observed scene within a preferably continuous subset of a plurality of wavelength bands A, B or C. One or more of the wavelength bands may be at least partly overlapping.

In one example, wavelength band A is selected as 7-9 μm and wavelength band B is selected as 9-15 μm, where the first infrared (IR) imaging system. 613 is configured to capture gas IR images in the form of IR image data values/pixel values, representing infrared radiation emitted from an observed scene within 7-8.6 μm, and where the second infrared (IR) imaging system 614 is configured to capture background IR images in the form of IR image data values/pixel values, representing infrared radiation emitted from an observed scene within 9-12 μm.

Further Examples of Wavelength Bands

Table 1 shows examples of ranges of wavelength bands for different gases that may be used in embodiments described herein. So for example and as shown in the table, embodiments of a method or a device as described herein may be devised for operating on CO2 and would in this example have a high absorption wavelength band A in the range of 4,2 μm-4,6 μm and a low absorption filter B in the range of 4,4 μm-4,6 μm.

TABLE 1

Examples of wavelength bands for different gases

| Gas | High absorption Wavelength band A | Low absorption Wavelength band B |
|---|---|---|
| Methane 1 | 3.2 μm-3.6 μm | 3.4 μm-3.6 μm |
| Methane 2 | 7.0 μm-9.0 μm | 8.5 μm-9.0 μm |
| CO2 | 4.2 μm-4.6 μm | 4.4 μm-4.6 μm |
| CO + N20 | 4.52 μm-4.87 μm | 4.67 μm-4.87 μm |
| Refrigerants | 8.0 μm-9.0 μm | 8.6 μm-9.0 μm |
| SF6 | 10.3 μm-11.1 μm | 10.7 μm-11.1 μm |

Spatial Sensor Configuration

FIG. 7a shows a schematic view of infrared sensors 6132, 6142 in a thermal imaging device 170 (cf. FIG. 6) configured to capture a gas IR image and a background IR image according to one or more embodiments. This can also be referred to as a spatial sensor configuration. A first infrared (IR) imaging system 613 (cf. FIG. 6), comprised in the thermal imaging device 170, comprises an image sensor 6132 configured to capture a gas IR image. The sensor 6132 is configured to capture infrared radiation within a high absorption wavelength band A. The first infrared (IR) imaging system 613 optionally comprises an optical gas filter 710 in the optical path of the sensor 6132 configured with a passband of infrared radiation within said high absorption wavelength band A. A second infrared (IR) imaging system 614 (cf. FIG. 6), comprised in the thermal imaging device 170, comprises an image sensor 6142 configured to capture a background IR image. The sensor 6142 is configured to capture infrared radiation within a low absorption wavelength band B. The second infrared (IR) imaging system 614 optionally comprises a background optical filter 720 in the optical path of the sensor 6142 configured with a passband of infrared radiation within said low absorption wavelength band B.

The sensor 6132, comprised in the first infrared (IR) imaging system 613, is configured to capture a gas IR image simultaneously, substantially simultaneously, or with a time interval, with the sensor 6142, comprised in the second infrared (IR) imaging system 613, capturing a background IR image.

In one or more embodiments, the processor 612 is adapted to send control data to the first infrared (IR) imaging system to trigger the sensor 6132 to capture infrared radiation within the high absorption wavelength band A, and/or is adapted to send control data the second infrared (IR) imaging system to trigger the sensor 6142 to capture infrared radiation within the low absorption wavelength band B.

In one or more embodiments comprising one or more optical filters, the processor 612 is adapted to send control data to the first infrared (IR) imaging system to configure the gas optical filter 710 with a pass band equal to wavelength band A and adapted to send control data to the second infrared (IR) imaging system to configure the background optical filter 720 with a pass band equal to wavelength band B. A combination of controllable sensor and controllable optical filter are provided in one or more embodiments.

Temporal Sensor Configuration

FIG. 7b shows a schematic view of an infrared sensor 6132, 6142 in a thermal imaging device 170 (cf. FIG. 6) configured to capture a gas IR image and a background IR image according to one or more embodiments. This can also be referred to as a temporal sensor configuration. A first infrared (IR) imaging system 613, comprised in the thermal imaging device 170, comprises an image sensor 6132 configured to capture a gas IR image at time $T_0$ and a background IR image at time $T_1$. In one or more embodiments, the sensor 6132 is at time $T_0$ configured to capture infrared radiation within a high absorption wavelength band A. The first infrared (IR) imaging system 613 optionally comprises an optical filter 710 in the optical path of the sensor 6132 configured at time $T_0$ with a passband of infrared radiation equal to a high absorption wavelength band A and configured at time $T_1$ with a passband of infrared radiation equal to a low absorption wavelength band B.

In one or more embodiments, the processor 612 is adapted to send control data to the first infrared (IR) imaging system to configure the captured wavelength band of the sensor 6132 to the high absorption wavelength band A and to trigger the capturing of a gas IR image at time $T_0$, and to configure the captured wavelength band of the sensor 6132 to the low absorption wavelength band B and to trigger the capturing of a gas IR image at time $T_1$. Typically, there is a short time lapse between the time $T_0$ and the time $T_1$, suitably selected to reconfigure the sensor for different wavelength bands.

In one or more embodiments comprising one or more optical filters, the processor 612 is adapted to send control data to the first infrared (IR) imaging system to configure the optical filter 710 with a pass band equal to the high absorption wavelength band A at time $T_0$ and to configure the optical filter 710 with a pass band equal to the low absorption wavelength band B at time $T_1$. A combination of controllable sensor and controllable optical filter are provided in one or more embodiments also in a temporal sensor configuration.

Method Embodiments

As described above one or more embodiments relate to an improved system and method of imaging quantified gas, in particular passive infrared imaging of gas occurring in a scene. The gas is imaged based on a difference in an estimated gas temperature $T_G$ and an estimated background temperature $T_B$. Consequently, a greater difference between $T_G$ and $T_B$ will result in a greater contrast in the imaged gas in relation to background. When the estimation of $T_G$ and $T_B$ are improved, the sensitivity of the imaging system is improved and smaller amounts of gas can be detected and optionally imaged. With improved sensitivity of the imaging system, the contrast of the imaged gas is improved, e.g. in a gas-absorption-path-length image representing the length of the path of radiation from the scene background 110 through a gas occurrence in the scene.

Embodiments described herein thus increase the sensitivity of gas detection in an image, and thereby the contrast, by an improved and dynamic selection of a high absorption wavelength band A and a low absorption wavelength band B, e.g. based on previously captured gas and background IR images.

Figure 8:
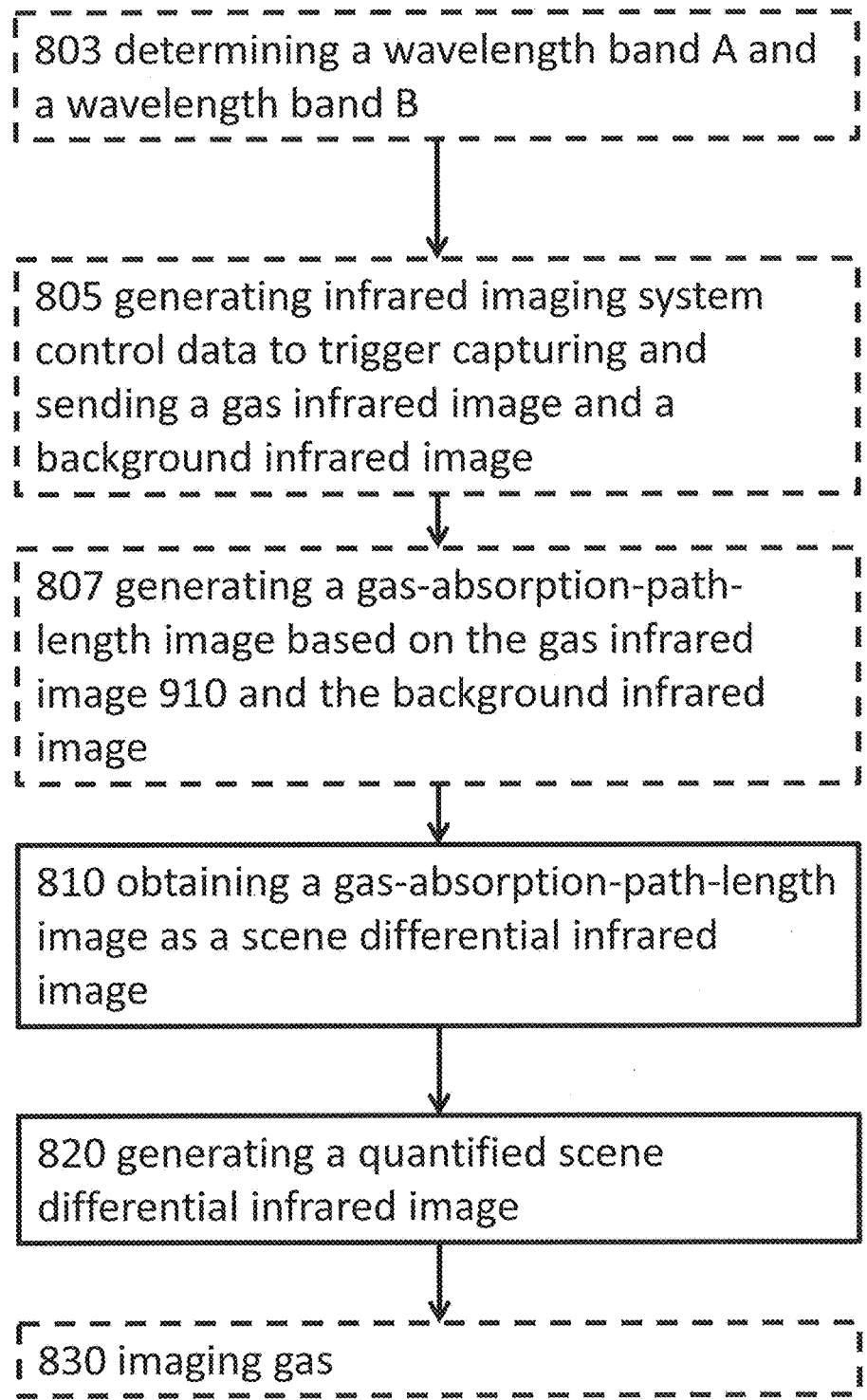
FIG. 8 is a block diagram showing method embodiments, in accordance with one or more embodiments of the disclosure.

FIG. 8 illustrates embodiments of a method of quantifying gas in a thermal imaging device, in accordance with one or more embodiments. Gas is quantified by obtaining a gas-absorption-path-length image as a scene difference infrared image and generating a quantified scene difference infrared image based on the scene difference infrared image and a predefined gas-quantifying relation, where an increased contrast has been obtained by finding an improved balance between gas detection signal to noise ratio by determining a first, high absorption wavelength band A and a second, low absorption wavelength band B.

In one or more embodiments, a method to quantify gas in a thermal imaging device 170, said method comprises a selection of:

Step 810: Obtaining a gas-absorption-path-length image as a scene difference infrared image based on a gas infrared image 910 and a scene background infrared image 920 substantially depicting the same scene 110.

In one example, the gas-absorption-path-length image is obtained by retrieving it from memory 615. In yet one example, the gas-absorption-path-length image is obtained generating a gas-absorption-path-length image by a processor 612.

Step 820: Generating a quantified scene difference infrared image based on said scene difference infrared image and a predefined gas-quantifying relation 180.

In one example a quantified scene difference infrared image is generated by retrieving the gas-absorption-path-length image/scene difference infrared image and a predefined gas-quantifying relation 180 from memory 615. Each pixel in the quantified scene difference infrared image is determined by applying the gas-quantifying relation 180 to each pixel in the scene difference infrared image.

In one or more embodiments, the gas-quantifying relation 180 describes the relation between scene difference infrared image pixel values 181,900 and quantified scene difference infrared image pixel values 182 in the form of a concentration length product expressed in parts per million*meter or ppm*m, e.g. by multiplying the gas concentration by the gas-absorption path length 1601.

On one example, scene difference infrared image pixel values are generated by generating image pixel values as a selection of:

gas infrared image pixel value $A_{row,\,col}$-background infrared image pixel value $B_{row,\,col}$; or background infrared image pixel value $B_{row,\,col}$-gas infrared image pixel value $A_{row,\,col}$, The pixel values are for example represented by temperature values in degrees Celsius or Kelvin and the predefined gas-quantifying relation 180 is a look-up table, e.g. as depicted in relation to tables 1-4 in FIG. 17. For each scene difference infrared image pixel values indicating a temperature there is a corresponding concentration length product, expressed in parts per million*meter or ppm*m. I.e. in this example each pixel in the quantified scene difference infrared image$_{row,\,col}$=GQR (scene difference infrared image$_{row,\,col}$).

In one or more embodiments, the gas-quantifying relation 180 is generated by:

measuring a first set of quantified scene difference infrared image pixel values 182 for: known gas concentration, gas-absorption path length 1601, gas temperature $T_G$ and background temperature $T_B$; and expanding said first set to a second larger set by applying curve fitting techniques.

In one example, quantified scene difference infrared image pixel values 182 are measured using absorption spectroscopy in a controlled environment. A first set of measurement values or quantified scene difference infrared image pixel values 182 are obtained by varying the gas concentration and the gas-absorption path length 1601, e.g. by replacing sample glass vials with known gas concentration and known gas-absorption path length and monitoring the gas temperature $T_G$ and background temperature $T_B$.

In one or more embodiments, the step 810 of obtaining a gas-absorption-path-length image further comprises and/or is preceded by:

Step 803: Determining, by a processor 612, a first, high absorption wavelength band A 510 and a second, low absorption wavelength band B 520 to improve contrast in a generated gas-absorption-path-length image based on estimated image noise, a predetermined absorption spectrum of the gas 241, an estimated gas temperature TG 121 and an estimated background temperature TB 122.

Step 805: Generating, by the processor 612, infrared imaging system control data to trigger the capturing, by a first infrared imaging system 613, of a gas infrared image of a scene comprising intensity of infrared radiation within high absorption wavelength band A 510 and to trigger, by a second infrared imaging system 614, the capturing of a background infrared image of the scene comprising intensity of infrared radiation within wavelength band B 520.

Step 807: Generating a gas-absorption-path-length image based on the gas infrared image 910 and the background infrared image 920.

Preferably, as in one or more embodiments, high absorption wavelength band A 510 includes an absorption wavelength band G 505 from the absorption spectrum 241. Further, low absorption wavelength band B 520 may at least partially overlap high absorption wavelength band A 510. Examples of determining high absorption wavelength band A 510 and low absorption wavelength band B 520 are further described in relation to FIG. 12-16.

In one example, infrared imaging system control data, comprising data indicating high absorption wavelength band A 510 and low absorption wavelength band B 520 and triggering information, is sent to a first and a second infrared imaging system 613,614. The control data is configured to control preferably the first infrared imaging system 613 to capture and return a gas infrared image of a scene comprising intensity of infrared radiation within high absorption wavelength band A 510. The control data is further configured to trigger preferably the second infrared imaging system 614 to capture a background infrared image of the scene comprising intensity of infrared radiation within low absorption wavelength band B 520. In one example the first and second infrared imaging system 613,614 are integrated in the thermal imaging device 170. In yet one example the first and second infrared imaging systems 613,614 are external to the thermal imaging device 170.

In one or more embodiments, wherein the estimated image noise comprises Noise Equivalent Temperature Difference, the quantified scene difference infrared image pixel values 182 comprise temperature values, e.g. in degrees Celsius or Kelvin. In one example, the Noise Equivalent Temperature Difference NETD is measured as Root Mean Square RMS noise, $\Delta U_{noise}$, which is the noise voltage measured as a Root Mean Square value of the imaging systems video channel and then converted to the corresponding temperature difference in degrees Celsius or Kelvin.

In one or more embodiments, the high absorption wavelength band A 510 is determined with a lower endpoint 5101 in the interval of [6-7.8 μm]-[8-9.6 μm]] and wherein wavelength band A 510 is determined with a higher endpoint 5502 in the interval of [8-9.6 μm].

For uncooled thermal imaging devices to be used with an acceptable image noise level, the high absorption wavelength band A and low absorption wavelength band B have to be quite broad compared to cooled cameras, as uncooled cameras have less sensitivity and a higher thermal noise contribution. As the filter regions are quite broad not only absorption of for example the gas methane is present in the filter region but also water vapor. This means that water vapor has to be quantified as well as the gas, here methane. One way to achieve this is to have an additional third, water related wavelength band C 530 determined and spectrally filtered where only water vapor absorbs the radiation, e.g. by capturing a water infrared image 1030 comprising infrared radiation within wavelength band C. This is used in order quantify water vapor and then use this measurement to generate a composite spectrum to quantify gas, for example methane. Another example to compensate for water vapor is to measure the humidity in the air and the distance from the thermal imaging device 170 to the background scene 110 and assume the humidity is the same over this whole distance. The concentration length can then be estimated as measured humidity in ppm*distance from the thermal imaging device 170 to the background scene 110, thereby calculating the concentration length of water vapor in ppm×m.

One or more embodiments, further comprises:
determining, by a processor 612, a third, water related wavelength band C 530 to improve contrast in a generated gas-absorption-path-length image based on a predetermined water absorption spectrum, wherein the water related wavelength band C 530 includes at least a local maximum of the water absorption spectrum and excludes both the high absorption wavelength band A 510 and the low absorption wavelength band B 520.

Such embodiments typically further comprises:
generating infrared imaging system control data to trigger the capturing of a water infrared image 1030, by a first imaging system 613 or a second imaging system 614, of the scene 110, wherein the water infrared image comprises intensity of infrared radiation within wavelength band C 530.

In these embodiments, generating a quantified scene difference infrared image is further based on the water infrared image 1030. A gas infrared image 510 in accordance with these embodiments comprises intensity of infrared radiation within the high absorption wavelength band A and the background infrared image 520 comprises intensity of infrared radiation within the low absorption wavelength band B. A water infrared image 1030 comprises intensity of infrared radiation within the wavelength band C An example on how quantified scene difference infrared image pixel values with a gas infrared image, a background infrared image and a water infrared image are determined is further described in relation to FIG. 10 below.

For visualization of a gas in a scene, a method, in accordance with one or more embodiments, further comprises:
Step 830: imaging gas based on pixel values in the quantified scene difference infrared image. To enable a user to understand the information in the quantified scene difference infrared image, an image is generated to comprise a visual representation and selectively presenting it on a display 618 in the thermal imaging device or in a computing device connected to the thermal imaging device such as a tablet computer, a smartphone, a laptop or a desktop computer. The visual representation may for example be based on the quantified scene difference infrared image and a palette.

In one example, generating a visual representation comprises mapping quantified scene difference infrared image data values or pixel values of each pixel to a palette used to present the corresponding pixel displayed on a display, e.g. using grey-scale or colors selected from a color model. In yet another example of step 830, imaging gas is performed by generating a visual representation of the quantified scene difference infrared image using false coloring, wherein generating a visual representation further comprises mapping data values or pixel values in the quantified scene difference infrared image to a palette and displaying the visual representation. In yet an example, the palette comprises colors or greyscales from a predefined color model. In yet an example, wherein imaging gas further comprises displaying the display gas infrared image on a display in the thermal imaging device or on a display comprised in an external device.

Figure 9:
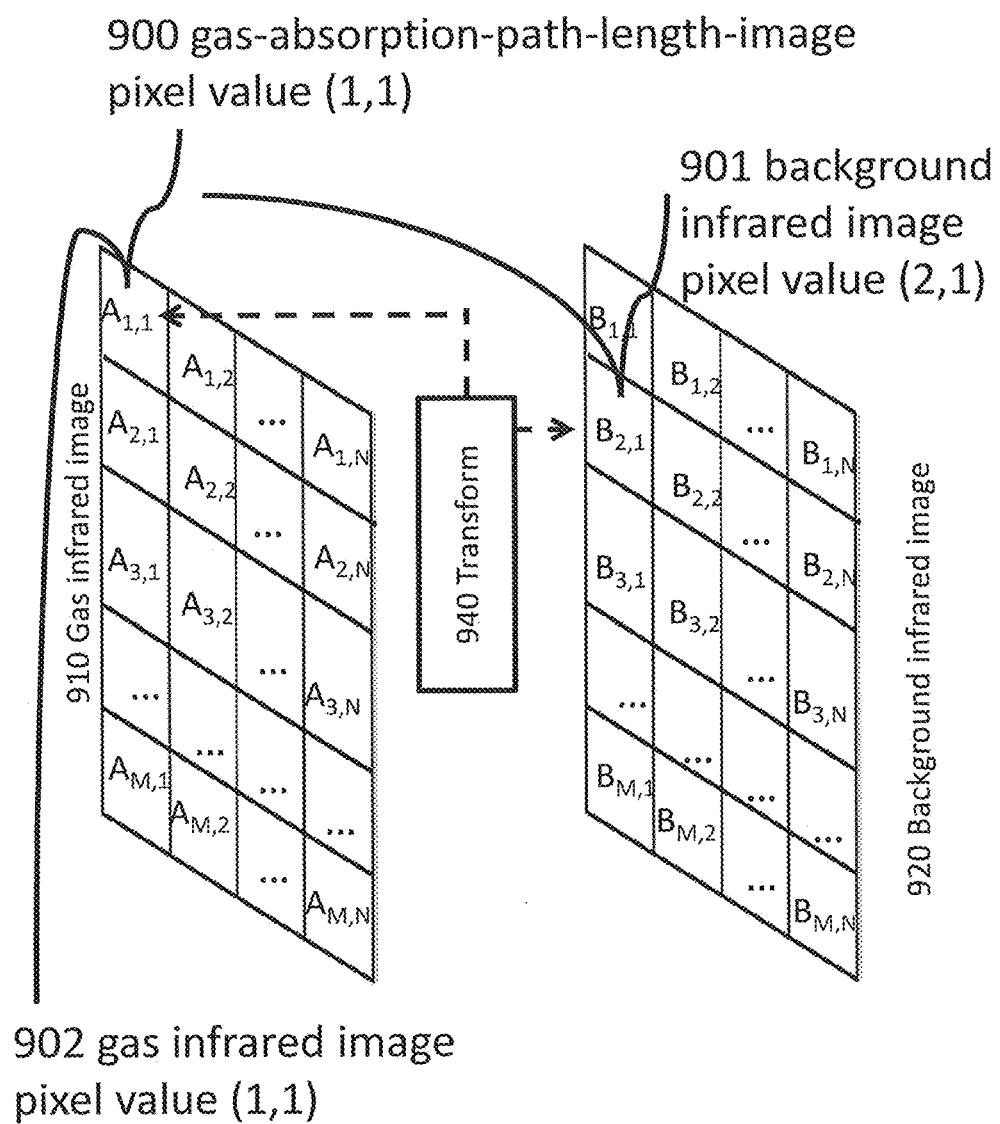
FIG. 9 shows how a gas-absorption-path-length image is generated a thermal imaging device comprising a first infrared imaging system and a second infrared imaging system, in accordance with one or more embodiments of the disclosure.

FIG. 9 shows how a gas-absorption-path-length image is generated in accordance with one or more embodiments, where a thermal imaging device 170 comprising a first infrared imaging system 613 and a second infrared imaging system 614, e.g. as depicted in FIG. 6. The optical axis and the field of view FOV may differ leading to different parallax errors and different FOV size. To ensure that pixel values comprised in the gas infrared image and pixel values comprised in the background infrared image represent the same part of the scene 110 before combining them to a pixel value comprised in the gas-absorption-path-length image, they are registered or transformed into one coordinate system through a transform 940, e.g. intensity-based registration, feature-based registration by using linear or elastic transformations. In one example, the gas-absorption-path-length image pixel value 900 is determined based on signal difference and a gas-absorption-path-length image pixel value 900 is determined as image pixel $value_{1,1}$=gas infrared image pixel value 902 $A_{1,1}$-background infrared image pixel value 901 $B_{2,1}$. In yet an example, the pixel value is determined based on signal difference and the gas-absorption-path-length image pixel value is determined as image pixel $value_{1,1}=B_{2,1}-A_{1,1}$. In yet an example the gas-absorption-path-length image pixel values are determined based on the ratio of gas versus no gas and the gas-absorption-path-length image pixel $value_{1,1}=B_{2,1}/A_{1,1}$. In yet an example the gas-absorption-path-length image pixel values are determined based on the ratio of gas versus no gas and the gas-absorption-path-length image pixel $value_{1,1}=A_{1,1}/B_{2,1}$.

Figure 10:
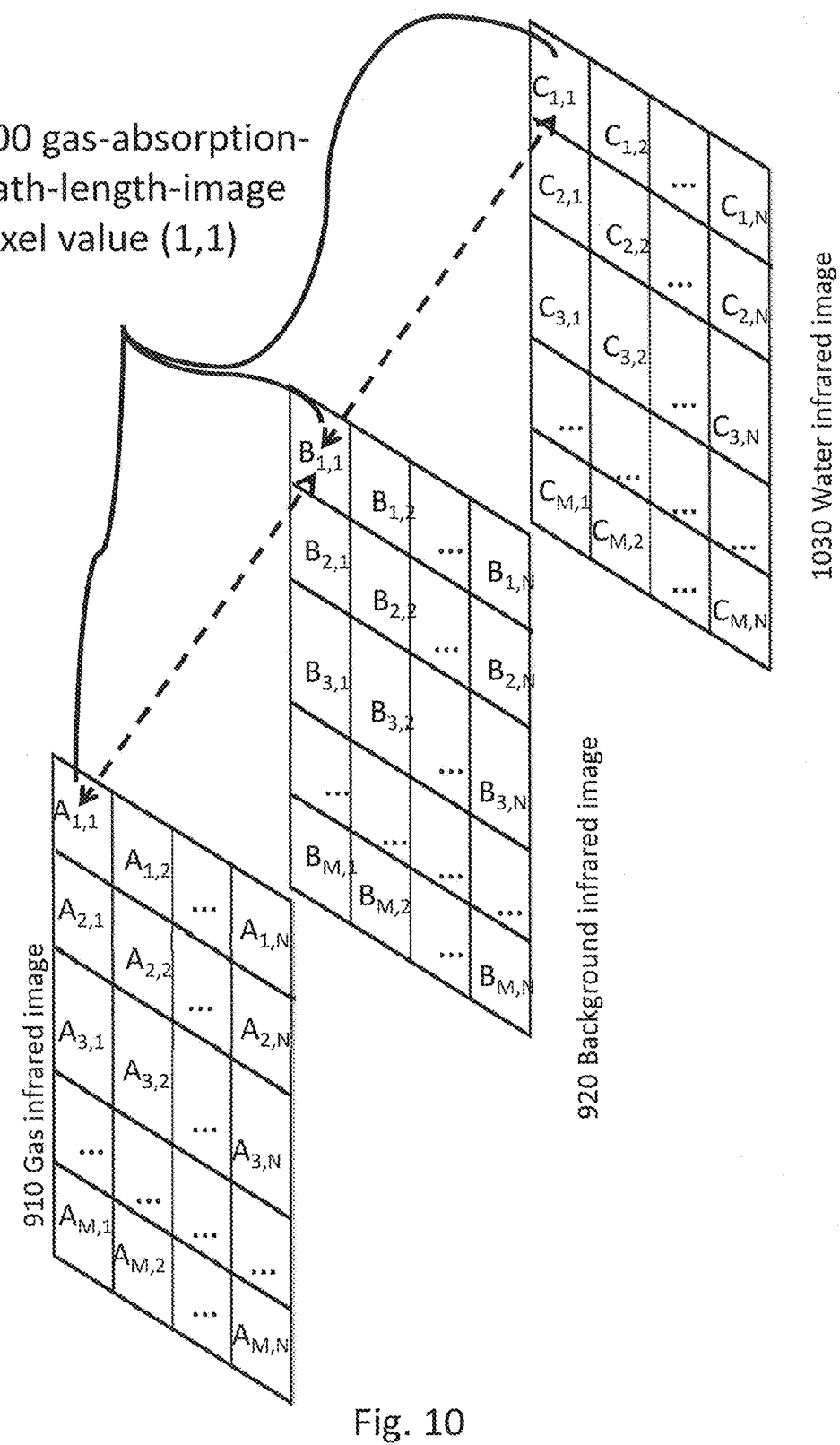
FIG. 10 shows how a gas-absorption-path-length image is generated in by compensating for water attenuation of infrared radiation, in accordance with one or more embodiments of the disclosure.

FIG. 10 shows how a gas-absorption-path-length image is generated, in accordance with one or more embodiments, by compensating for water attenuation of infrared radiation. In embodiments, the sensitivity to detecting gas and thus contrast in the gas-absorption-path-length image is further improved by generating the gas-absorption-path-length image further based on a water infrared image 1030. In embodiments, a wavelength band C is determined to improve contrast in a generated gas-absorption-path-length image based on a predetermined water absorption spectrum, wherein wavelength band C includes at least a local maximum of the water absorption spectrum and preferably excludes both high absorption wavelength band A and low absorption wavelength band B. By determining the attenuation of infrared radiation in a water related wavelength band where the absorption spectrum for water has a at least a local maximum and where the gas show no or very low attenuation of infrared radiation, a measure of water attenuation in a water wavelength band C, can be approximated to be valid also for high absorption wavelength band A and low absorption wavelength band B, thus the contribution of water attenuation can be compensated for. In embodiments, water wavelength band C is indicated in data comprised in infrared imaging system control data sent to the infrared imaging system. In embodiments a water infrared image 1030 is captured by the first or second infrared imaging system 613, 614 triggered by the control data, wherein the water infrared image comprises intensity of infrared radiation within water wavelength band C. In embodiments, the processor 612 receives the water infrared image and generates an improved gas-absorption-path-length image based on a gas infrared image 910, a background infrared image 920 and the water infrared image 1030.

In embodiments, a gas-absorption-path-length image is generated by combining pixel values comprised in the gas infrared image 910, pixel values comprised in the background infrared image 920 and pixel values comprised in the water infrared image 1030. In yet an example the gas-absorption-path-length image pixel values are determined based on the signal difference and the gas-absorption-path-length image pixel $value_{1,1}=A_{1,1}-B_{1,1}-C_{1,1}$. In yet an example the gas-absorption-path-length image pixel values are determined based on the signal difference and the gas-absorption-path-length image pixel $value_{1,1}=A_{1,1}-B_{1,1}+C_{1,1}$. In yet an example the gas-absorption-path-length image pixel values are determined based on the signal difference and the gas-absorption-path-length image pixel $value_{1,1}=B_{1,1}-A_{1,1}-C_{1,1}$. In yet an example the gas-absorption-path-length image pixel values are determined based on the signal difference and the gas-absorption-path-length image pixel $value_{1,1}=B_{1,1}-A_{1,1}+C_{1,1}$. In yet an example the gas-absorption-path-length image pixel values are determined based on the signal difference and the gas-absorption-path-length image pixel $value_{1,1}=A_{1,1}-C_{1,1}/B_{1,1}$. In yet an example the gas-absorption-path-length image pixel values are determined based on the signal difference and the gas-absorption-path-length image pixel $value_{1,1}=C_{1,1}-A_{1,1}/B_{1,1}$.

Aligning

Since the gas and background IR image 910,920 may be captured at different instances in time the thermal imaging device might be moved in a way such that the offset, direction and rotation around the optical axis differ between a gas IR image and a background IR image. Similarly, in one or more embodiments with multiple infrared imaging systems 613, 614, the orientation of optical axis of the first infrared imaging system 613 and the second infrared imaging system 614 might differ. This results in an optical phenomenon known as parallax distance error, parallax pointing error and parallax rotation error. Due to these parallax errors, the captured view of the real world scene might differ between IR images. In order to combine the gas infrared image and the background infrared image, the images must be adapted so that an adapted gas IR image and an adapted background IR image, representing the same part of the scene, is obtained, compensating for the different parallax errors and FOV size. This processing step is referred to as image registration or alignment of the first image and the second image, i.e. the process of transforming different sets of data into one coordinate system through a transform 940. Registration or alignment can be performed according to any method known to a skilled person in the art, e.g. intensity based, feature-based registration using linear or elastic transformations.

Displaying visualizing an image, IR image, quantified scene difference infrared image or gas-absorption-path-length image As thermal images by nature are generally low contrast and noisy, the captured IR image or gas-absorption-path-length image may be subjected to various imaging processing in order to improve the interpretability of the image before displaying it to a user. Examples of such image processing is correction with IR temperature calibration data parameters, low pass filtering, registration of multiple successive IR image or gas infrared images and averaging to obtain an averaged IR image or gas infrared image or any other IR image or gas infrared image processing operation known to a person skilled in the art. As infrared radiation is not visible to the human eye there are no natural relations between the captured IR image's, quantified scene difference infrared image or gas-absorption-path-length image gas infrared image's data values of each pixel in the image and the greyscale or the colors displayed on a display.

Therefore, an information visualization process referred to as false coloring or pseudo coloring is used to map image data values or pixel values of each pixel in animage, such as an IR image, quantified scene difference infrared image or gas-absorption-path-length image, to a palette used to present the corresponding pixel displayed on a display, e.g. using grey-scale or colors.

A palette is typically a finite set of color or grey-scale representations selected from a color model for the display of images or visual representations of IR images, quantified scene difference infrared image or gas-absorption-path-length image, i.e. a pre-defined palette represents a finite set of grayscale or color values of a color model displayable on a display thereby making it visible to the human eye. Mapping of image data values of each pixel in an image, such as an IR image, quantified scene difference infrared image or gas-absorption-path-length image, to a palette used to present the corresponding pixel of a visual representation of said image displayed on a display is typically performed by applying a pre-determined relation. Such a pre-determined relation typically describes a mapping from image data values or pixel values to said pre-defined palette, e.g. a palette index value with an associated color or grey-scale representation selected from a color model. The gas IR image, quantified scene difference infrared image or gas-absorption-path-length image is typically displayed to an intended user based on the image data values or pixel values of each pixel in an image, such as an IR image, quantified scene difference infrared image or gas-absorption-path-length image. Optionally IR temperature calibration data parameters, a predefined palette representing a finite set of grayscale or color values of a color model displayable on a display and a pre-determined relation describing a mapping from infrared image data values or gas-absorption-path-length image pixel values to said pre-defined palette.

Use Case Embodiments

Figure 11:
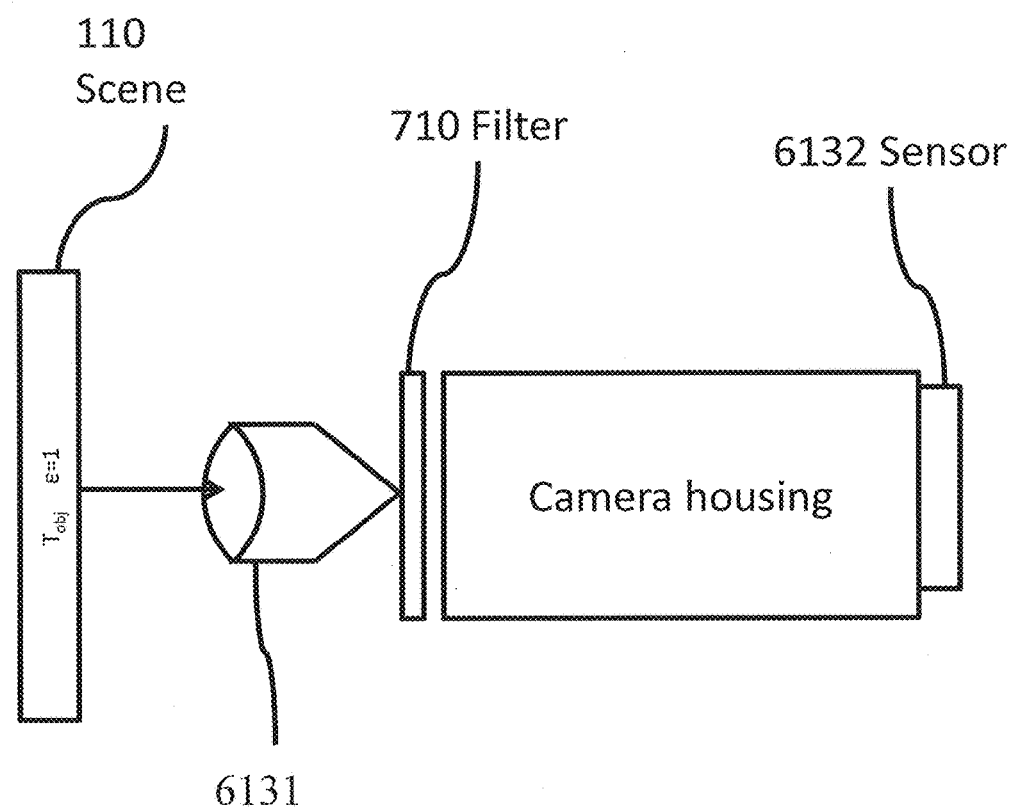
FIG. 11 shows the use of two cameras filtered to image different spectrum regions and enabling the quantification of leaking gas, in accordance with one or more embodiments of the disclosure.

In FIG. 11, there is shown an illustration of a camera in a system and method in accordance with one or more embodiments. In an example with the use of two cameras filtered to image different spectrum regions, images are generated used to quantify leaking gas. One camera detector will be filtered to a high absorption wavelength band A where the gas has strong absorption lines or high absorption of infrared radiation in the absorption spectrum, so that the camera will change signal when gas is present in the image. The other camera will be filtered to a low absorption wavelength band B where the gas has very weak or in this case almost no absorption lines or low absorption of infrared radiation in the absorption spectrum. In this manner the camera is used as a reference to see the background temperature without gas. By taking the temperature difference between images from camera filtered to detect high absorption wavelength A and low absorption wavelength B only the gas will be visible and other phenomenon but gas will be reduced.

A model to optimally choose filter 710,720 positions or filter tunings with regard to signal and noise affected by these filter 710,720, in accordance with one or more embodiments, is explained as follows:

The signal S is calculated by taking the exitance or measured emission of infrared radiation from the object, $W_{obj}$ added with the exitance or measured emission of infrared radiation from the background, $W_{bg}$.

The signal S is calculated by taking the exitance from the object, $W_{obj}$, added with the exitance from the background, $W_{bg}$.

$$W_{bg} = (1 - \sin^2\theta)\int M(T_{cam}, \lambda)R_{det}(\lambda) + \sin^2\theta \int M(T_{filter}, \lambda)R_{det}(\lambda)1 - \tau_{filter} \quad \text{Eq. 1}$$

$$W_{obj} = \sin^2\theta \int_{cuton}^{cutoff} M(T_{obj}, \lambda)R_{det}(\lambda)\tau_{obj}\tau_{filter} \quad \text{Eq. 2}$$

$$\sin(\theta) = \frac{1}{2F} \quad \text{Eq. 3}$$

Where F is the F-number and is specified by the objective.

$$S = W_{bg} + W_{obj} \quad \text{Eq. 4}$$

Noise

The noise of thermal cameras is often measured in NETD which stands for Noise Equivalent Temperature Difference. This is measured by the RMS noise, $\Delta$Unoise, which is the noise voltage measured as a Root Mean Square value of the cameras video channel and then converting it to the corresponding temperature difference. NETD can then be written as follows:

$$NETD = \frac{\Delta U_{noise}}{S'T} \quad \text{Eq. 5}$$

Here S'T is the derivative of the signal measured by the detector at a temperature T. By taking the derivative of Eq. 4 with regard to T, S'T can be calculated. This derivative is evaluated at 30° C. since this is a common temperature for measuring NETD. Since the detector noise, $\Delta$Unoise, in Eq. 5 is assumed to be the same with and without filter 710,720 this is regarded as a constant. The NETD is calculated by inserting a known NETD without filter and calculating S'T with τ_filter=1 to simulate a case without filtering and comparing it to NETD with the transmission of a filter. With this in mind Eq. 6 becomes:

$$\Delta U_{noise} = \frac{NETD_{known}}{S'T, \tau_{filter}=1} = \frac{NETD_{filtered}}{S'T} \quad \text{Eq. 6}$$

$$NETD_{filtered} = \frac{NETD_{known} * S'T}{S'T, \tau_{filter}=1} \quad \text{Eq. 7}$$

For uncooled cameras to be used, the filter 710,720 regions have to be much broader compared to cooled cameras because uncooled cameras have less sensitivity and a higher thermal noise contribution from the optical path to the sensor/detector 6132,6142. As the filter 710,720 regions are quite broad not only absorption of gas as for example methane is present in the filter region but also water vapor. This means that water vapor has to be quantified as well as the gas, here methane. One way to achieve this is to have an additional third region spectrum filtered where only water vapor absorbs the radiation, e.g. wavelength band C 530. This is used in order quantify water vapor and then use this measurement to generate a composite spectrum to quantify methane. The other way is to measure the humidity in the air and the length to the background and assume the humidity is the same over this whole distance, and then calculate the concentration length of water vapor in ppm×m. For the calculation of signal difference between gas and no gas the temperature of gas is needed and this is assumed be the same as the temperature in the air. This means that the air temperature has to be measured as well. The input values, to calculate signal difference with gas and no gas needed, are the background temperature, the concentration length of water vapor, concentration length of methane gas and the temperature of the gas. With two different cameras that has different gain and offset values it is important to normalize the outputs so that the cameras will measure the same temperature. This is done by calibrating the cameras with the filters 710,720 and beam splitter against blackbody radiators at different known temperatures. With the measurement points of known temperatures corresponding to raw values a curve fit algorithm can be used as a function translating the raw values to temperature. Another way to quantify the gas is to practically make a calibration where different known concentrations are measured at varying distances with varying relative humidity to see how the signal in the cameras change. With these values a function can be generated that depends on signal change, distance and humidity.

Signal/Noise and Implementation

With changing cuton or lower endpoint 5101 of high absorption wavelength band A and cutoff or higher endpoint 5102 of high absorption wavelength band A, the influence of the gas can be optimized with regard to NETD and signal difference. Both the ratio between gas and no gas, and difference in signal were simulated with the motivation that theoretically the signal difference should be maximized without regard for emissivity change. Although the ratio between gas and no gas should be high because when using two cameras the normalization between the signals won't be perfect and result in a ratio difference. The chosen simulated cuton wavelengths range from 6-7.8 µm and cutoff from 8-9.6 µm with 0.2 µm steps. This is because the methane absorption peak is centered around 7.7 µm and the band pass filter 710,720 should be close to this absorption peak.

Figure 12:
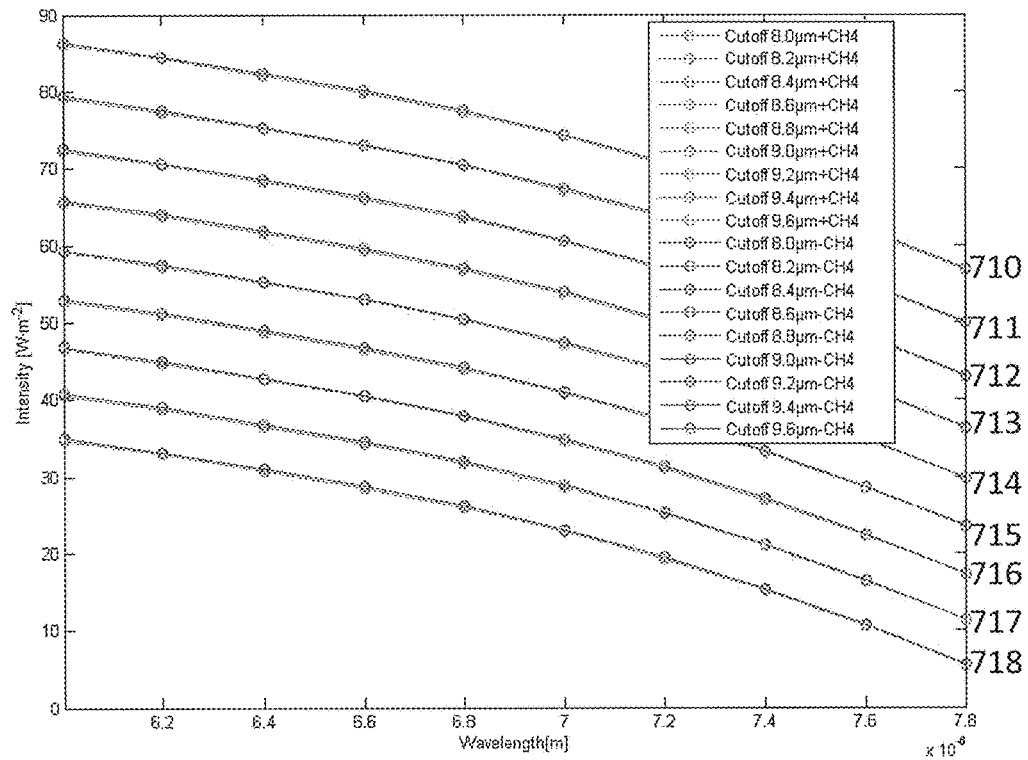
FIG. 12 shows the resulting signal with changing filter 710,720 cuton and cutoff, i.e. lower endpoint and higher endpoint of a wavelength band, in accordance with one or more embodiments of the disclosure.

FIG. 12 shows the resulting signal with changing filter 710,720 cuton and cutoff, i.e. lower endpoint and higher endpoint of a wavelength band, from a cutoff at 8 µm 710 to a cutoff at 9.6 µm 718.

Figure 13:
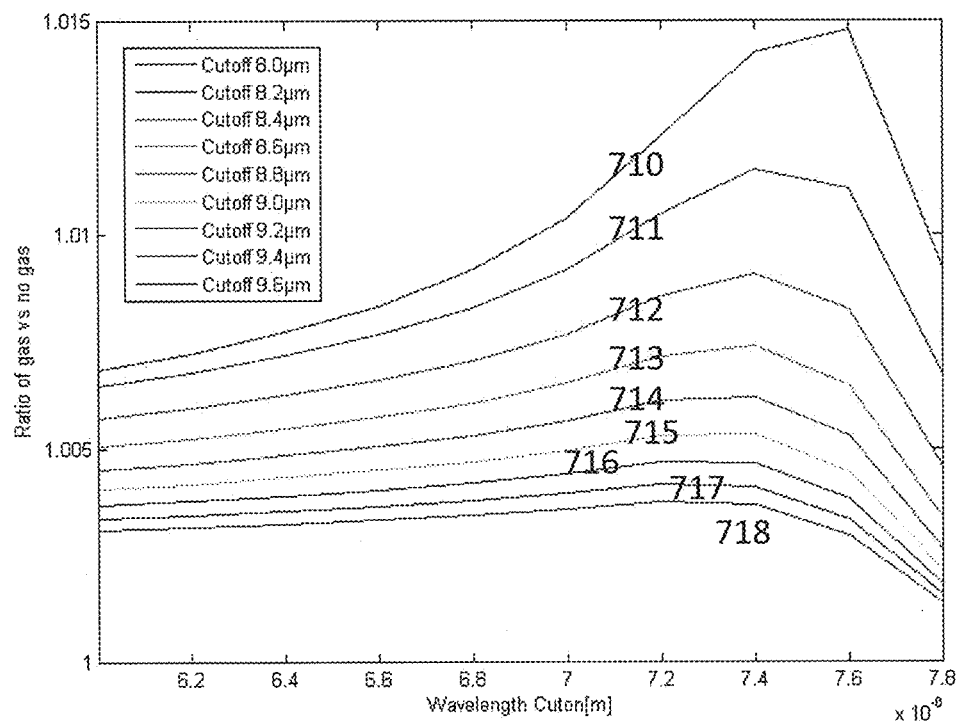
FIG. 13 shows simulated signal ratio with and without an exemplifying methane gas, in accordance with one or more embodiments of the disclosure.

FIG. 13 shows the simulated signal gas or no gas ratio with and without methane gas in the simulation. As can be seen the ratio of the signal will decrease with increasing bandwidth of the band pass filter, thus the wavelength band from a cutoff at 8 µm 710 to a cutoff at 9.6 µm 718, although the signal difference will remain constant. The cuton wavelength goes up to 7.8 µm to show the decrease in signal difference as the cuton exceeds the absorption peak.

Figure 14:
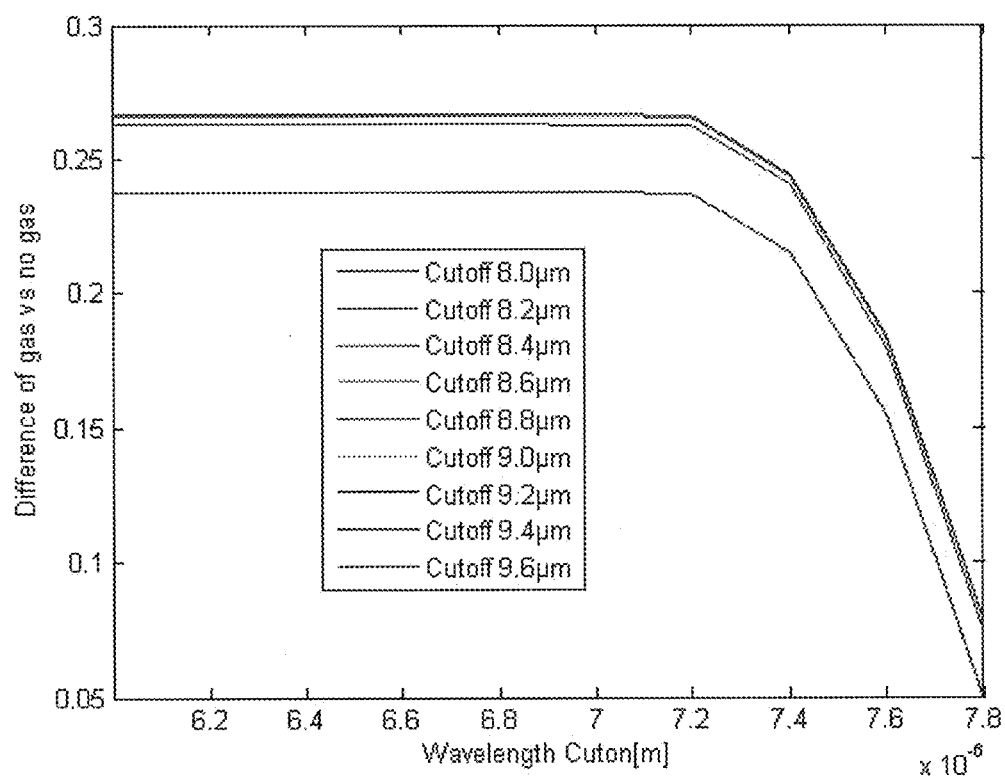
FIG. 14 shows a simulated signal difference with and without methane gas, in accordance with one or more embodiments of the disclosure.

FIG. 14 shows the simulated signal difference with and without methane gas in the simulation. As can be seen the ratio of the signal will decrease with increasing bandwidth of the band pass filter, thus the wavelength band from a cutoff at 8 µm to a cutoff at 9.6 µm, although the signal difference will remain constant. The cuton wavelength goes up to 7.8 µm to show the decrease in signal difference as the cuton exceeds the absorption peak.

Figure 15:
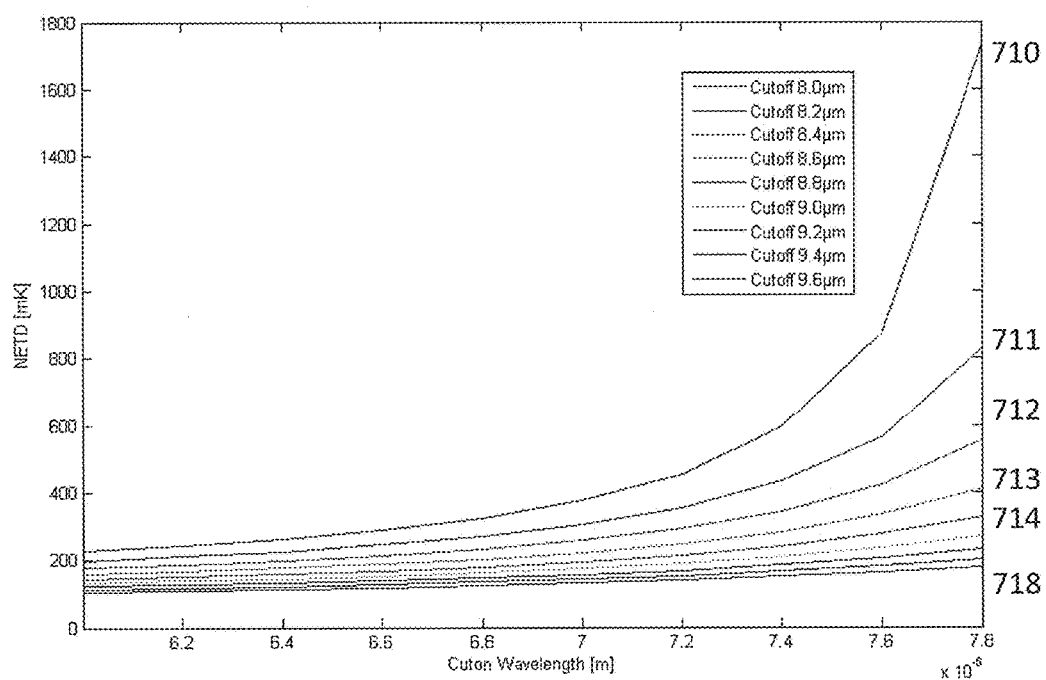
FIG. 15 shows simulated noise NETD with changing wavelength band A, in accordance with one or more embodiments of the disclosure.

FIG. 15 shows an embodiment of the disclosure, where simulated NETD with changing filter band-pass bandwidth from a cutoff at 8 µm 710 to a cutoff at 9.6 µm 718. As can be seen the noise NETD is increased with decreasing filter bandwidth.

These simulations are used to decide the A filter region, or to determine wavelength band A, for the camera that should see the gas. Two different ideas are presented as one focuses on the signal difference and one on the ratio of gas vs. no gas. Since the ratio of gas vs. no gas counteracts the NETD the region was chosen to have a reasonably low NETD while the ratio is as high as possible. The region was chosen for a cuton at 7 µm and cutoff at 8.6 µm which gives a NETD of 221 mK and a ratio of 1.007 for 1000 ppmm methane.

When looking at signal differences instead of ratio, e.g. background infrared image pixel value-gas infrared image pixel value or background infrared image pixel value/gas infrared image pixel value it's clear to see from FIG. 13 that the signal difference is unchanged when filters exceed the absorption lines of the gas or where the absorption spectrum includes a local maxima. With this in mind the NETD can be maximized by having a large filter bandwidth so for this a cuton at 7 µm was chosen since the signal is unaffected for lower cuton wavelengths and the cutoff is limited by the detector.

To choose the filter wavelengths of the B region, or to determine the low absorption wavelength band B, where no or very little gas absorption should be present or where the absorption spectrum includes a local minimum the filter positions are simulated with a cutoff at 15 µm to simulate the cutoff of the camera system response and cuton ranging from 8 µm to 10.5 µm because this is where the absorption of methane will decrease to a limit where no absorption is present. This is shown in FIG. 16.

Figure 16:
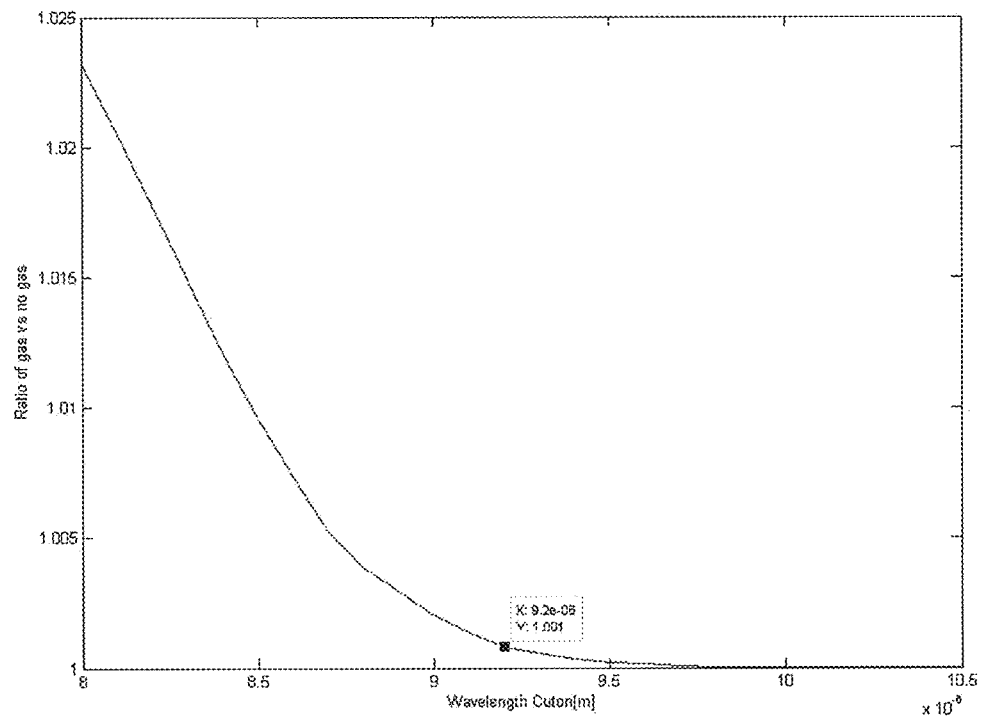
FIG. 16 shows a simulation of ratio of gas vs no gas for changing cuton and a fix cutoff at 15 μm for wavelength band A and B, in accordance with one or more embodiments of the disclosure.

FIG. 16 Shows an embodiment of the invention where a simulation of ratio of gas vs no gas for changing cuton and a fixed cutoff at 15 µm. The methane concentration length used for this simulation is 1*107 ppmm. The chosen cuton wavelength is 9.2 µm since there's very low absorption ratio for this cuton wavelength when simulation for a very concentrated and big gas cloud.

Quantification

FIG. 17 shows various embodiments of the Gas-Quantifying Relation 180 of the present disclosure, e.g. in table 1-4.

In one example, by simulating the temperature difference with spectrum containing different concentration lengths a function to determine the gas concentration length, Gas-Quantifying Relation 180, is determined. This was done with known background temperature and gas temperature. In one example, the blackbody used as background was set to 70° C. To simulate the temperature difference measured background temperature was measured with the camera and also the gas cell was measured with the camera to realize the gas temperature. For the BP filter the background temperature was measured to 79.4±0.1° C. and the gas cell was measured to 30.9±0.2° C. This gave simulated values for the temperature with regard to gas absorption.

TABLE 1

Simulated temperatures for different concentration-lengths for the BP filter. The table values from table 2 were plotted in MATLAB and a curve fit of the 3rd order was used to get a function that would translate the temperature values into concentration-lengths.

| Concentration-length | Simulated temperature |
| --- | --- |
| 1000 ppmm | 73.0159° C. |
| 5000 ppmm | 70.3222° C. |
| 10000 ppmm | 68.4830° C. |
| 20000 ppmm | 66.1178° C. |
| 30000 ppmm | 64.4258° C. |
| 60000 ppmm | 60.9544° C. |

TABLE 1-continued

Simulated temperatures for different concentration-lengths for the BP filter. The table values from table 2 were plotted in MATLAB and a curve fit of the 3rd order was used to get a function that would translate the temperature values into concentration-lengths.

| Concentration-length | Simulated temperature |
|---|---|
| 120000 ppmm | 56.9215° C. |
| 200000 ppmm | 53.7470° C. |

Measured temperatures for different gas concentration-lengths are presented below, with their calculated concentration lengths and known concentration lengths.

TABLE 2

Measured temperatures with calculated concentration-lengths compared to known concentration-length for the BP filter.

| Known concentration-length $CL_K$ | Measured temperature T | Measured concentration-length $CL_M$ | $CL_M/CL_K$ |
|---|---|---|---|
| 5 000 ppmm | 68.7° C. | 9 090 ppmm | 1.82 |
| 10 000 ppmm | 66.7° C. | 17 190 ppmm | 1.72 |
| 20 000 ppmm | 63.8° C. | 34 270 ppmm | 1.71 |
| 30 000 ppmm | 61.7° C. | 52 020 ppmm | 1.73 |
| 60 000 ppmm | 57.9° C. | 102 180 ppmm | 1.70 |
| 120 000 ppmm | 53.7° C. | 201 630 ppmm | 1.68 |

The same procedure was done for the LP 7000 filter. For this filter the background temperature was measured to 73.5±0.1° C. and the gas cell temperature was measured to 24.3±0.1° C. This gave simulated temperature values with regard to gas absorption shown in table 4.

TABLE 3

Simulated temperatures for different concentration-lengths for the LP7000 filter

| Concentration-length | Simulated temperature |
|---|---|
| 1000 ppmm | 73.159° C. |
| 5000 ppmm | 70.3222° C. |
| 10000 ppmm | 68.4830° C. |
| 20000 ppmm | 66.1178° C. |
| 30000 ppmm | 64.4258° C. |
| 60000 ppmm | 60.9544° C. |
| 120000 ppmm | 56.9215° C. |
| 200000 ppmm | 53.7470° C. |

As for the BP filter these values are used to estimate a curve fit of the 3rd order was used to calculate the concentration length of measured temperatures.

Known concentration-length CLK Measured temperature T Measured

TABLE 4

Measured temperatures with calculated concentration-lengths compared to known concentration-length for the LP7000 filter.

| Known concentration-length $CL_K$ | Measured temperature T | Measured concentration-length $CL_M$ | $CL_M/CL_K$ |
|---|---|---|---|
| 5 000 ppmm | 66.7° C. | 48 630 ppmm | 9.73 |
| 10 000 ppmm | 66.1° C. | 72 860 ppmm | 7.29 |
| 20 000 ppmm | 64.9° C. | 156 040 ppmm | 7.80 |
| 30 000 ppmm | 64.5° C. | 198 770 ppmm | 6.63 |
| 60 000 ppmm | 63.2° C. | 416 940 ppmm | 6.95 |
| 120 000 ppmm | 61.9° C. | 811 570 ppmm | 6.76 |

As the measured values for of 416 940 ppmm and 811 570 ppmm are outside the range from the simulated concentration-length fit these may be unreliable.

Other Embodiments

The processor of described thermal imaging devices is, in accordance with one or more embodiments, configured to perform a selection of any or all of the method steps described herein that are associated with processing of captured IR images or gas-absorption-path-length images comprising image data values or pixel values, such as selection of data values/pixel values, mapping of temperature values associated with the data values/pixel values to color and/or grayscale values, assigning each pixel of a frame of IR data values a representation value from a preselected color model, e.g. based on the associated temperature value of said pixel, and other operations described herein.

In one or more embodiments, there is provided a computer-readable medium on which is stored:

non-transitory information for performing a method according to any of the embodiments described herein; and/or non-transitory information configured to control a processor/processing unit to perform any of the steps or functions of embodiments described herein.

In one or more embodiments, there is provided a computer program product comprising code portions adapted to control a processor to perform any of the steps or functions of any of the embodiments described herein. Software in accordance with the present disclosure, such as program code portions and/or data, can be stored in non-transitory form on one or more machine-readable mediums. It is also contemplated that software identified herein can be implemented using one or more general purpose or specific purpose computers and/or computer systems, networked and/or otherwise.

Where applicable, one or more embodiments provided by the present disclosure can be implemented using hardware, software, or combinations of hardware and software. Also where applicable, the various hardware components and/or software components set forth herein can be combined into composite components comprising software, hardware, and/or both. Where applicable, the various hardware components and/or software components set forth herein can be separated into sub-components comprising software, hardware, or both. In addition, where applicable, it is contemplated that software components can be implemented as hardware components, and vice-versa. Where applicable, the ordering of various steps described herein can be changed, combined into composite steps, and/or separated into sub-steps to provide features described herein.

The foregoing disclosure is not intended to limit the present invention to the precise forms or particular fields of use disclosed. It is contemplated that various alternate embodiments and/or modifications to the present invention, whether explicitly described or implied herein, are possible in light of the disclosure. Accordingly, the scope of the invention is defined only by the claims.

The invention claimed is:

1. A method comprising:
obtaining a gas-absorption-path-length image for a gas in a scene based on a gas infrared image of the scene captured in response to radiation received in a high absorption wavelength band A for the gas and a background infrared image of the scene captured in response to radiation received in a low absorption wavelength band B for the gas;
applying a predefined gas-quantifying relation to pixel values of the gas-absorption-path-length image; and
generating a quantified scene difference infrared image in response to the applying, wherein pixel values of the quantified scene difference infrared image correspond to concentrations of the gas in the scene.

2. The method of claim 1, wherein the gas-quantifying relation describes a relationship between the pixel values of the gas-absorption-path-length image and the pixel values of the quantified scene difference infrared image in the form of a concentration length product expressed in parts per million*meter (ppm*m).

3. The method of claim 1, wherein the gas-quantifying relation is generated by operations comprising:
measuring a first set of quantified scene difference infrared image pixel values for known gas concentrations, gas-absorption path lengths, gas temperatures, and background temperatures; and
expanding the first set to a second larger set by applying a curve fitting technique, the gas-quantifying relation comprising a relationship between the pixel values of the gas-absorption-path-length image and the second larger set of quantified scene difference infrared image pixel values.

4. The method of claim 1, wherein:
the obtaining comprises determining the high absorption wavelength band A for the gas and the low absorption wavelength band B for the gas;
the high absorption wavelength band A includes an absorption wavelength band G from an absorption spectrum for the gas; and
the low absorption wavelength band B at least partially overlaps the high absorption wavelength band A.

5. The method of claim 4, wherein the obtaining further comprises:
generating infrared imaging system control data to control the capturing, by an infrared imaging system, of the gas infrared image of the scene and of the background infrared image of the scene; and
generating the gas-absorption-path-length image based on the gas infrared image and the background infrared image.

6. The method of claim 4, wherein:
the high absorption wavelength band A and the low absorption wavelength band B are determined based on at least estimated image noise comprising a Noise Equivalent Temperature Difference (NETD); and
the pixel values of the quantified scene difference infrared image comprise temperature values.

7. The method of claim 4, wherein:
the high absorption wavelength band A is determined with a lower endpoint in a range between and including about 6 μm and 7.8 μm; and
the high absorption wavelength band A is determined with a higher endpoint in a range between and including about 8 μm and 9.6 μM.

8. The method of claim 4, further comprising:
determining a water related wavelength band C to improve contrast in the generated gas-absorption-path-length image based on a predetermined water absorption spectrum, wherein the water related wavelength band C includes at least a local maximum of the water absorption spectrum and excludes the high absorption wavelength band A and the low absorption wavelength band B; and
wherein the gas-absorption-path-length image exhibits an increased contrast further based on a water infrared image of the scene captured in response to radiation received in the water related wavelength band C; and
wherein the generating of the quantified scene difference infrared image is further based on the water infrared image.

9. A device comprising:
an infrared (IR) imaging system configured to capture:
a gas infrared image of a scene captured in response to radiation received in a high absorption wavelength band A for a gas; and
a background infrared image of the scene captured in response to radiation received in a low absorption wavelength band B for the gas;
a memory; and
a processor communicatively coupled to the IR imaging system and the memory, the processor being configured to:
obtain a gas-absorption-path-length image for a gas in the scene based on the gas infrared image and the background infrared image;
apply a predefined gas-quantifying relation to pixel values of the gas-absorption-path-length image; and
generate a quantified scene difference infrared image in response to application of the gas-quantifying relation, wherein pixel values of the quantified scene difference infrared image correspond to concentrations of the gas in the scene.

10. The device of claim 9, wherein the gas-quantifying relation describes a relationship between the pixel values of the gas-absorption-path-length image and the pixel values of the quantified scene difference infrared image in the form of a concentration length product expressed in parts per million*meter (ppm*m).

11. The device of claim 9, wherein the gas-quantifying relation is generated by operations comprising:
measuring a first set of quantified scene difference infrared image pixel values for known gas concentrations, gas-absorption path lengths, gas temperatures, and background temperatures; and
expanding the first set to a second larger set by applying a curve fitting technique, the gas-quantifying relation comprising a relationship between the pixel values of the gas-absorption-path-length image and the second larger set of quantified scene difference infrared image pixel values.

12. The device of claim 9, wherein the infrared imaging system is configured and/or controllable to:
capture the gas infrared image of the scene; and
capture the background infrared image of the scene.

13. The device of claim 12, wherein the infrared imaging system comprises:
a first infrared imaging system configured and/or controllable to capture the gas infrared image; and a second infrared imaging system configured and/or controllable to capture the background infrared image.

14. The device of claim 12, wherein:
the high absorption wavelength band A includes an absorption wavelength band G from an absorption spectrum for the gas; and
the low absorption wavelength band B at least partially overlaps the high absorption wavelength band A.

15. The device of claim 14, wherein:
the high absorption wavelength band A and the low absorption wavelength band B are determined based on at least estimated image noise comprising a Noise Equivalent Temperature Difference (NETD); and
the pixel values of the quantified scene difference infrared image comprise temperature values.

16. The device of claim 12, wherein:
the high absorption wavelength band A is determined with a lower endpoint in a range between and including about 6 μm and 7.8 μm; and
the high absorption wavelength band A is determined with a higher endpoint in a range between and including about 8 μm and 9.6 μm.

17. The device of claim 12, wherein the processor is further configured to obtain the gas-absorption-path-length image by operations comprising:
generating control data to control the capturing of the gas infrared image and the background infrared image by the infrared imaging system; and
generating the gas-absorption-path-length image based on the gas infrared image and the background infrared image.

18. The device of claim 12, wherein:
the infrared imaging system is further configured and/or controllable to capture a water infrared image of the scene captured in response to radiation received in a water related wavelength band C;
the water related wavelength band C includes at least a local maximum of a water absorption spectrum and excludes the high absorption wavelength band A and the low absorption wavelength band B; and
the processor is further configured to generate the quantified scene difference infrared image further based on the water infrared image.

19. The device of claim 18, wherein the water related wavelength band C is determined based on the water absorption spectrum so as to improve contrast in the generated gas-absorption-path-length image.

20. A non-transitory computer-readable medium storing instructions which, when executed by a processor of a device, cause the device to:
obtain a gas-absorption-path-length image for a gas in a scene based on a gas infrared image of the scene captured in response to radiation received in a high absorption wavelength band A for the gas and a background infrared image of the scene captured in response to radiation received in a low absorption wavelength band B for the gas;
apply a predefined gas-quantifying relation to pixel values of the gas-absorption-path-length image; and
generate a quantified scene difference infrared image in response to application of the gas-quantifying relation, wherein pixel values of the quantified scene difference infrared image correspond to concentrations of the gas in the scene.

* * * * *